US011297285B2

(12) United States Patent
Pierce

(10) Patent No.: US 11,297,285 B2
(45) Date of Patent: Apr. 5, 2022

(54) DENTAL AND MEDICAL LOUPE SYSTEM FOR LIGHTING CONTROL, STREAMING, AND AUGMENTED REALITY ASSISTED PROCEDURES

(71) Applicant: Sean Solon Pierce, Tustin, CA (US)

(72) Inventor: Sean Solon Pierce, Tustin, CA (US)

(73) Assignee: Sean Solon Pierce, Tustin, CA (US)

( * ) Notice: Subject to any disclaimer, the term of this patent is extended or adjusted under 35 U.S.C. 154(b) by 0 days.

(21) Appl. No.: 16/936,272

(22) Filed: Jul. 22, 2020

(65) Prior Publication Data

US 2021/0306599 A1    Sep. 30, 2021

Related U.S. Application Data

(60) Provisional application No. 63/001,069, filed on Mar. 27, 2020.

(51) Int. Cl.
*H04N 7/18* (2006.01)
*G06F 3/14* (2006.01)
(Continued)

(52) U.S. Cl.
CPC ............ *H04N 7/185* (2013.01); *A61B 90/35* (2016.02); *A61B 90/361* (2016.02); *A61C 1/088* (2013.01); *G02B 27/0172* (2013.01); *G02C 7/088* (2013.01); *G02C 11/04* (2013.01); *G06F 3/1454* (2013.01); *G06K 9/00228* (2013.01); *H04N 5/2256* (2013.01); *H05B 47/125* (2020.01);
(Continued)

(58) Field of Classification Search
None
See application file for complete search history.

(56) References Cited

U.S. PATENT DOCUMENTS 6,528,954 B1 * 3/2003 Lys ...................... A61N 5/0616
315/291
7,008,074 B1 * 3/2006 Halm ................... H05B 47/195
362/105
(Continued)

FOREIGN PATENT DOCUMENTS

CN    104579401 A  *  4/2015  ........... H04B 1/3827
CN    106569337 A  *  4/2017
(Continued)

*Primary Examiner* — Reza Aghevli
(74) *Attorney, Agent, or Firm* — Shook, Hardy & Bacon, L.L.P.

(57) ABSTRACT

In various examples, a dental and medical loupe system for lighting control, streaming, and augmented reality (AR) assisted procedures is provided. Facial recognition algorithms and/or inertial measurement unit (IMU) sensors may be used to determine when a light disposed on eye-glasses of a wearer should be activated. As a result, instead of requiring a medical practitioner to manually turn on and off the light source, facial recognition may be used to determine when the dentist is looking toward a face of a patient, and to turn on the light when a face is present and off when a face is not present. In addition, some examples leverage augmented reality (AR) functionality to overlay patient and procedure information on one or more lenses of eye-glasses worn by a practitioner to allow for an un-occluded view of the actual location where the procedure is being performed.

20 Claims, 13 Drawing Sheets

(51) Int. Cl.

| | |
|---|---|
| *G02B 27/01* | (2006.01) |
| *H05B 47/125* | (2020.01) |
| *G02C 11/04* | (2006.01) |
| *A61B 90/35* | (2016.01) |
| *A61C 1/08* | (2006.01) |
| *G06K 9/00* | (2006.01) |
| *H04N 5/225* | (2006.01) |
| *G02C 7/08* | (2006.01) |
| *A61B 90/00* | (2016.01) |
| *A61B 90/50* | (2016.01) |

(52) U.S. Cl.
CPC .. *A61B 2090/502* (2016.02); *A61B 2562/0219* (2013.01); *G02B 2027/014* (2013.01); *G02B 2027/0138* (2013.01); *G02B 2027/0178* (2013.01); *H04N 5/2253* (2013.01)

(56) References Cited

U.S. PATENT DOCUMENTS

| | | | |
|---|---|---|---|
| 7,433,505 B2 | 10/2008 | Yoo et al. | |
| 7,842,052 B2 | 11/2010 | Mueller et al. | |
| 7,860,289 B2 | 12/2010 | Yoo et al. | |
| 8,068,169 B2 | 11/2011 | Chang | |
| 9,805,691 B2 * | 10/2017 | Umehara | G02B 27/017 |
| 10,394,029 B2 * | 8/2019 | Ayres | G02B 27/0172 |
| 2005/0231599 A1 * | 10/2005 | Yamasaki | H04N 9/8042 |
| | | | 348/207.99 |
| 2007/0014347 A1 * | 1/2007 | Prechtl | H04N 13/194 |
| | | | 375/240.01 |
| 2007/0098237 A1 * | 5/2007 | Yoo | G16H 30/40 |
| | | | 382/128 |
| 2007/0182812 A1 * | 8/2007 | Ritchey | H04N 5/23238 |
| | | | 348/36 |
| 2008/0204589 A1 * | 8/2008 | Chang | A61B 90/35 |
| | | | 348/373 |
| 2009/0033588 A1 * | 2/2009 | Kajita | G06T 19/006 |
| | | | 345/2.3 |
| 2010/0149323 A1 * | 6/2010 | Yoo | G16H 20/40 |
| | | | 348/66 |
| 2012/0127284 A1 * | 5/2012 | Bar-Zeev | G06T 19/006 |
| | | | 348/53 |
| 2014/0085203 A1 * | 3/2014 | Kobayashi | G01S 19/14 |
| | | | 345/158 |
| 2014/0337634 A1 * | 11/2014 | Starner | G06F 21/32 |
| | | | 713/186 |
| 2015/0104013 A1 * | 4/2015 | Holman | H04L 63/0442 |
| | | | 380/243 |
| 2015/0106628 A1 * | 4/2015 | Holman | G06F 21/602 |
| | | | 713/189 |
| 2015/0271557 A1 * | 9/2015 | Tabe | H04N 21/6131 |
| | | | 725/14 |
| 2016/0062457 A1 * | 3/2016 | Kobayashi | G06F 1/163 |
| | | | 345/156 |
| 2016/0085266 A1 * | 3/2016 | Lee | G06F 3/1454 |
| | | | 348/240.2 |
| 2016/0188283 A1 * | 6/2016 | Sendai | G02B 27/017 |
| | | | 345/8 |
| 2016/0238236 A1 * | 8/2016 | Im | F21V 19/001 |
| 2017/0308157 A1 * | 10/2017 | Tsuda | G06F 3/011 |
| 2018/0217590 A1 * | 8/2018 | Kobayashi | G05D 1/0038 |
| 2018/0308451 A1 * | 10/2018 | Saur | G02B 27/0179 |
| 2019/0004316 A1 * | 1/2019 | Baek | G06F 3/0304 |
| 2019/0251354 A1 * | 8/2019 | Cork | A61B 1/00039 |
| 2019/0378305 A1 * | 12/2019 | Fitzgerald | H04N 19/167 |
| 2020/0089313 A1 * | 3/2020 | Himane | G06F 3/016 |
| 2020/0160057 A1 * | 5/2020 | Roxas | G06K 9/00671 |

FOREIGN PATENT DOCUMENTS

| | | | | |
|---|---|---|---|---|
| CN | 201610922097 A | * | 4/2017 | ............ G02B 27/01 |
| JP | 2020-198513 | * | 12/2020 | ............... H04N 5/64 |
| JP | 2020198513 A | * | 12/2020 | ............... H04N 5/64 |

* cited by examiner

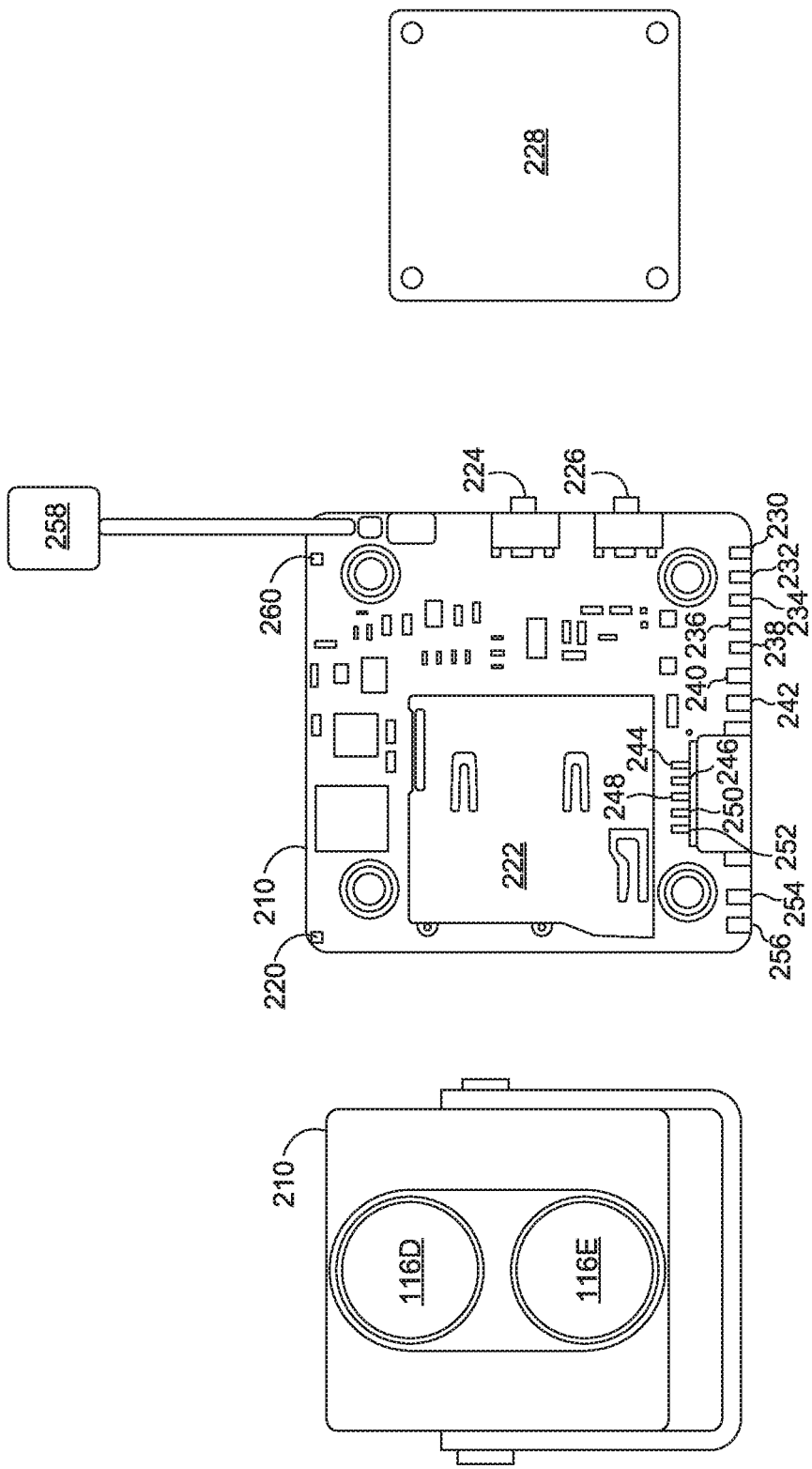

DENTAL AND MEDICAL LOUPE SYSTEM FOR LIGHTING CONTROL, STREAMING, AND AUGMENTED REALITY ASSISTED PROCEDURES

CROSS-REFERENCE TO RELATED APPLICATIONS

This application claims the benefit of U.S. Provisional Application No. 63/001,069, filed on Mar. 27, 2020, which is hereby incorporated by reference in its entirety.

BACKGROUND

Medical and dental professionals often wear eye-glasses, or other head worn devices, that may provide protection during their practice, provide increased magnification during procedures, or provide supplemental light to increase visibility. As an example, during dental practice, a dentist may turn on and off a light mounted on their eye-glasses to provide increased visibility within the oral cavity of a patient. These lights are often powered by a battery pack, and the on/off switch is generally located on the same. However, because the dentist must manually turn the light on and off using a switch, the light is often kept on for prolonged periods of time when not in use—such as when the dentist is looking away from the patient, has their eye-glasses removed and hanging from their neck, or otherwise forgets to turn off the light. As a result, the battery is often quickly depleted, requiring the dentist to use another battery pack or, where not available, wait for the battery pack to charge. In addition, when turning the light switch on and off or changing out the battery, the dentist is required to physically touch the light switch with his or her hands, which may cause unnecessary and unsanitary exchanging of pathogens—an issue that violates cleanliness and safety standards of dental practice.

In addition, although eye-glasses may be worn that include loupes to help increase magnification and thus visibility within the oral cavity, eye-glasses with loupes still do not help the dentist visualize regions of the oral cavity that are hard to see, or to visualize bone, gum, or other structures within the oral cavity that are obscured or otherwise concealed by gum tissue, the tongue, skin, or other tissue. For example, when performing dental implants, root canals, or other dental procedures, dentists often rely on x-rays and surgical guides which not only require extensive set-up (e.g., a first consultation for taking impressions, a follow up days later for confirming the surgical guide fits, additional radiation exposure, etc.), but are often not as accurate as desired. In addition, when performing these procedures using surgical guides, the dentist is often working on a region of the oral cavity that is obscured from view, and must rely on the surgical guide alone to execute the procedure. However, relying on the surgical guide alone without visual aid or confirmation may result in less-accurate procedures that may not be as permanent or long-lasting, and may also result in uneasiness or less confidence for the dentist performing the procedure. Additionally, a pre-fabricated surgical guide solely relies on proper treatment planning and, even where necessary, doesn't allow for any plan changes during surgery. As a result, the treatment plan may not be carried out as effectively as desired or may be halted or put on hold until a new surgical guide can be fabricated.

This same thought process may apply to other medical fields, such as general surgery, stent placements, pin, screw, or rod placements, joint replacement surgeries, and/or other medical procedures. For example, many surgical procedures rely on cameras inserted into the body for aid in visualizing the procedure (e.g., during laparoscopy) or rely on other instruments such as continuous X-ray machines to visualize the procedure (e.g., during angioplasty). However, these medical devices are often exorbitantly expensive, are unavailable, or are limited in availability such that urgent procedures may be postponed while waiting for their availability. Similarly, in dental or other medical procedures, robots may be relied upon to aid in conducting the procedure. However, in each of these procedure types—whether assisted by cameras, imaging technologies, robots, etc.—the medical practitioner relies on visuals that are either obscured (e.g., such as during dental implants) or distant from the patient (e.g., such as viewing a display screen showing a video from a camera, an X-ray, etc.). As such, the medical practitioner is unable to fully appreciate or clearly visualize the movement parts of the procedure with respect to the patient—thereby resulting in less than ideal operating conditions. Further, such as in angioplasty, the patient may undergo continuous radiation that may be detrimental to the health of the patient (e.g., by absorbing continuous radiation).

SUMMARY

Embodiments of the present disclosure relate to a dental and medical loupe system for lighting control, streaming, and augmented reality (AR) assisted procedures. Systems and methods are disclosed that use facial recognition algorithms and/or inertial measurement unit (IMU) sensors to determine when a light disposed on eye-glasses should be activated. In addition, systems and methods are disclosed that use AR functionality to aid in visualizing and guiding a medical practitioner through a medical procedure.

In contrast to conventional systems, such as those described above, one or more cameras disposed on eye-glasses—that may or may not include loupes—may be used to generate image data for use by a facial recognition algorithm. For example, instead of requiring a dentist to manually turn on and off the light source, facial recognition may be used to determine when the dentist is looking toward a face of a patient, and to turn on the light when a face is present and off when a face is not present. In addition, in some embodiments, and to further preserve battery life, the detection of a face of a person may be used to calibrate or zero-out IMU sensor(s), such that the IMU sensor(s) may then be relied upon for turning on and off the light source. As a result, the generation and/or transmission of image data may be suspended while the system relies on the IMU sensor(s). As a result, and in contrast to conventional systems, battery life may be preserved as the light source may only be activated when the dentist is facing the patient and infection control standards may be upheld as the dentist is not required to manually turn on and off the light switch.

In further contrast to conventional systems that rely solely on internal cameras, imaging technologies, robots, and/or other tools to assist in medical procedures, the systems and methods of the present disclosure use AR functionality to overlay patient and procedure information on one or more lenses of eye-glasses worn by a practitioner. For example, as an additional or alternative source of visualization information, an AR overlay may be generated and virtually projected in the field of view of the practitioner to aid the practitioner in performing a procedure. In a dental implant, for example, a patient's CT scan of one or more teeth may be virtually overlaid on the patient—e.g., on the patient's cheek using one or more markers or guides for reference—at a location that corresponds to the actual location of the one or more teeth. As such, the practitioner may be able to look toward the actual location of where the procedure is being performed, without visual occlusion, thereby increasing the accuracy of the procedure and increasing confidence of the practitioner with respect to the same—in a senses, giving the practitioner x-ray vision.

BRIEF DESCRIPTION OF THE DRAWINGS

The present systems and methods for lighting control, streaming, and augmented reality (AR) assisted procedures are described in detail below with reference to the attached drawing figures, wherein:

FIG. 2B is an example illustration of a housing associated with a head-worn device within a loupe system, in accordance with some embodiments of the present disclosure;

DETAILED DESCRIPTION

Systems and methods are disclosed related to a dental and medical loupe system for lighting control, streaming, and augmented reality (AR) assisted procedures. The disclosure is not intended to be limited to any particular medical field or practice, and may correspond to dentistry, general medical diagnosis and practice, surgical specialties, and/or any type of professional practice that may benefit from facial recognition based light source control and/or AR assisted visualizations. As such, even though the disclosure herein may be directed primarily to the dental or medical field, this is not intended to be limiting, and the systems and methods described herein may be used within additional or alternative practice fields or with different technologies altogether without departing from the scope of the present disclosure.

With reference to FIGS. 1A-1E, FIGS. 1A-1E illustrate an example loupe system(s) 102 for lighting control, streaming, and augmented reality assisted procedures, in accordance with some embodiments of the present disclosure. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory. In some non-limiting embodiments, one or more of the components of the loupe system(s) 102 may implement one or more of the components of example computing device 700 of FIG. 7, described in more detail herein. However, additional or alternative components other than those illustrated in FIG. 7 may be implemented without departing from the scope of the present disclosure. In addition, although referred to herein as a loupe system(s) 102, in some embodiments, no loupes may be implemented or included (e.g., eye-glasses or other head worn devices may be used without the use of loupes for magnification).

Figure 1A:
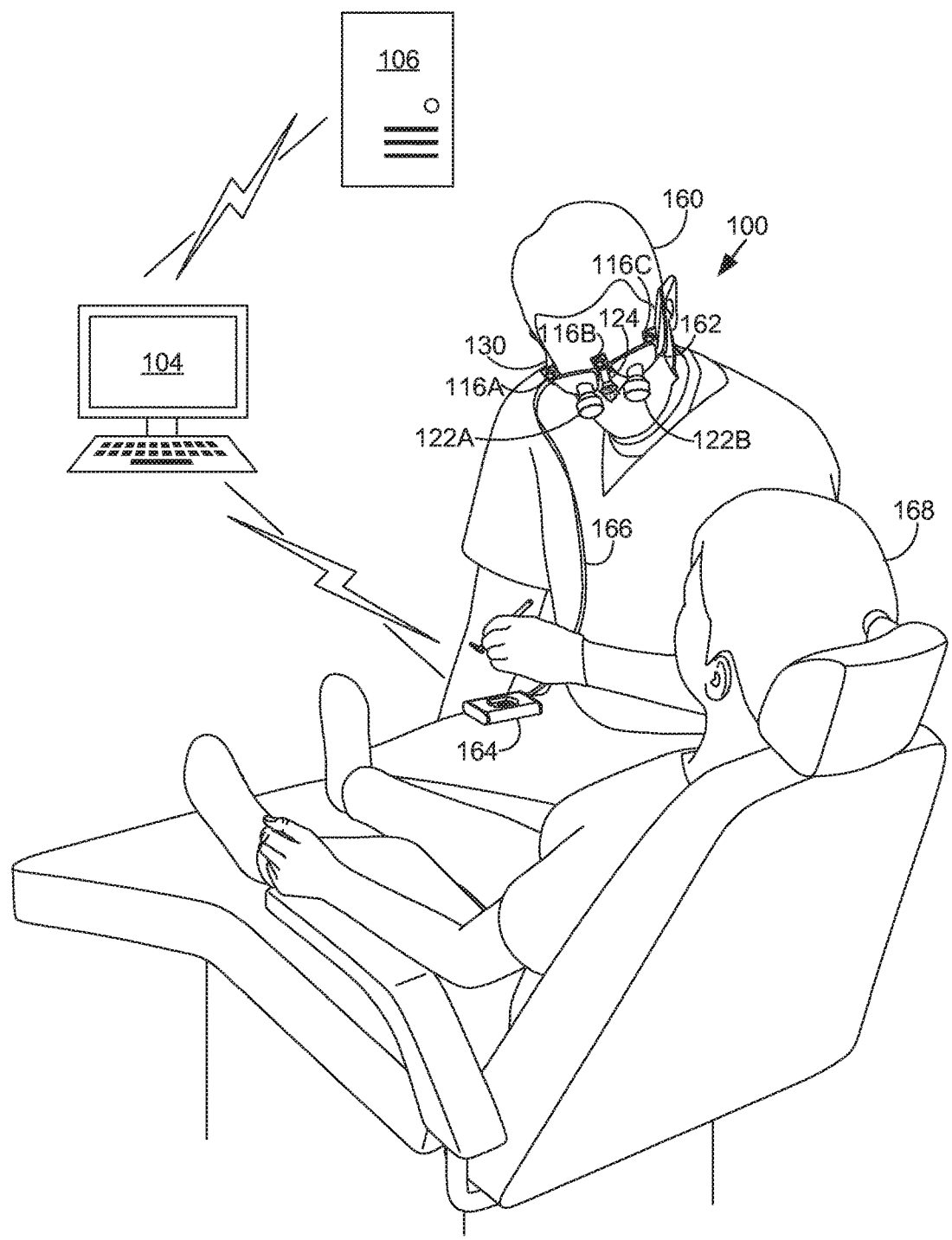
FIG. 1A is an example illustration of a loupe system in use during a dental procedure, in accordance with some embodiments of the present disclosure.

With reference to FIG. 1A, in some embodiments, the loupe system(s) 102 may be used for activating and/or deactivating a light(s) 124 (e.g., LED, halogen, CFL, etc.) disposed on a head-worn device 130—e.g., eye-glasses, a hat, a helmet, a visor, goggles, dental loupes, operating glasses, etc. For example, as described herein, conventional systems suffer from shortened battery life as a result of lights being left on, kept on when not in use, etc. In addition, conventional systems do not account for where the light is shining, such as in the eyes of a patient or assistant, and further require a user to physically turn on and off the light source using a button or switch—thereby causing transfer of germs and bacteria that may result in unaccounted for yet unsanitary operating or clinical conditions. As such, to account for each of these drawbacks of conventional systems, the present loupe system provides functionality for automatically turning on and/or off the light(s) 124 using one or more cameras 116, one or more IMUs 112—or sensors thereof—and/or one or more input/output (I/O) devices 126 (e.g., microphones, speakers, etc.).

For example, in some embodiments, the IMU(s) 112 may be used to turn on and/or off the light(s) 124. In such examples, the IMU(s) 112 may detect certain orientations, movements, or positions with respect to the head-worn device 130 (e.g., positions that indicate the user 160 is facing a person 168, or is otherwise in a position programmed to correspond to a light on position) that indicate that the light should be turned on, and similarly may detect certain orientations, movements, or positions that indicate the light should be turned off. For example, where a quick movement is detected, the light may be turned off, or where a lack of movement is detected for a threshold amount of time, the light may be turned on. In other examples, the IMU(s) 112 may be calibrated such that a zero position represents an orientation, movement, and/or position of the head-worn device 130 that is a light on position. As such, this position—and an operating degree of freedom therefrom—may be monitored to determine when the light should be on and when the light should be turned off. As a result, the light(s) 124 may be turned on and off depending on a variety of factors and based on data from the IMU(s) 112.

In at least one embodiment, a combination of the camera(s) 116 and the IMU(s) 112 may be used. For example, the image data from the camera(s) 116 may be analyzed to determine that a person 168—or a feature thereof—is present, and this confirmation may be used to calibrate or zero out the IMU(s) 112. As such, once the person 168 is detected, the camera(s) 116 may stop generating the image data and/or transmission of the image data to the local client device(s) 104 (where applicable) may be ceased, and the IMU(s) 112 may be used as the determiner of when to turn on and/or off the light. For example, where the IMU(s) 112 are zeroed out after a determination that a face of a person 168 is present, data from the IMU(s) 112 may be analyzed to determine whether certain movements, positions, and/or orientations are met that indicate the light should be turned off. Once a movement, position, and/or orientation is met that indicates the light should be turned off, the data from the IMU(s) 112 indicating that a subsequent movement, position, and/or orientation puts the head-worn device 130 back within a threshold of the zeroed out position may cause the light to be activated again. As such, once a person 168 or feature thereof is detected, and the IMU(s) 112 are zeroed or otherwise calibrated, the IMU(s) 112 may be used exclusively during the particular session and/or until a threshold amount of deviation is detected that prompts another determination of the presence of the person 168. This may help to further increase battery life. In some examples, the camera(s) 116 may be reactivated periodically—e.g., at an interval—to capture updated image data that may be analyzed to determine a presence of a person or feature thereof in order to recalibrate or zero-out the IMU(s) 112.

As an example, where a dentist is using the light(s) 124 to illuminate the mouth of the person 168, the movement of the dentist's head (or the head-worn device 130) upward a certain degree (e.g., 10 degrees, 15 degrees, etc.) from the zeroed position may align with the eyes of the person 168. In some embodiments, the degree of movement that corresponds to eyes of the person 168 may be individualized for each patient. For example, facial recognition, computer vision, machine learning, or other techniques may be leveraged to develop a zero or calibration point for the area of focus for a particular patient and/or for the degree of movement from a zero or calibration point at which the light should be turned off. As a result, the IMU(s) 112 may be calibrated for each individual function thereby increasing accuracy and scalability of implementation of the loupe system 102 across a wider range of patients or persons. As such, when a movement above this threshold in the upward direction is detected using the data from the IMU(s) 112, the light may be switched off, and when the dentist moves back toward the mouth of the person 168—and thus within the threshold—the light may be reactivated. Similarly, when looking downward away from the mouth, a larger threshold may be used (e.g., 20 degrees, 40 degrees, etc.) because the dentist may need to look for tools, cloths, napkins, or other items, as well as look at status information of one or more machines. In addition, because a movement downward likely will not result in shining the light(s) 124 in the eyes of the person 168, the downward threshold may be greater than the upward threshold. Other thresholds may be used for the left and right rotation or movement, such that a movement threshold in any direction may be put in place, and monitored in view of the data from the IMU(s) 112.

In some embodiments, the camera(s) 116 alone may be used to detect a person or a feature thereof. For example, image data generated by the camera(s) 116 may be analyzed by the loupe system(s) 102, the local client device(s) 104 (e.g., a computer, laptop, phone, tablet, etc.), and/or server(s) 106 to determine when a person or feature thereof is present, and the light(s) 124 may be activated and deactivated based on this determination. As such, the image data captured by the camera(s) may be analyzed using one or more computer vision, facial recognition, and/or other detection algorithms to determine the presence of a person 168, a face of a person 168, another feature of a person 168, and/or the like. In any embodiment where image data is analyzed, the facial recognition or other recognition may be person specific. For example, the particular patient and corresponding stored facial recognition data may be determined such that the activation or deactivation of the light(s) 124 is only for the particular person. As such, if the face of a nurse, assistant, friend or family member, or other person other than the patient is detected, this detection may not cause activation of the light(s) 124. However, detecting the face of another person other than the patient may prompt deactivation of the light(s) 124.

In some examples, the image data may be continually generated and/or analyzed (e.g., a 30 frames per second (FPS), 60 FPS, etc.), while in other examples, the image data may be generated periodically (e.g., 1 FPS, 2 FPS, etc.) such as to preserve battery life. Depending on the particular procedure, certain indicators may be identified or detected using the image data to determine when the light(s) 124 should be turned on and off. For example, during general dentistry, when a mouth of a person is at a particular location within the image data (e.g., centered, within a central region, within a portion of the image illuminated by light from the light(s) 124, etc.) the light may be activated. When the mouth is at a different location, or the light from the light(s) 124 is determined to be at or near the eyes of the person 168, the light may be deactivated. These determinations may be determined using one or markers on the person, guides on the person, or features of the person as reference. For example, where a feature or marker is identified at a particular location in an image represented by the image data (e.g., above a certain pixel row), the light may be deactivated as this location may indicate that the light(s) 124 is likely shining in the eyes of the person. Similarly, when a person is not detected at all—of a face or other features are not detected—the light may be deactivated. As such, as a user 160 looks away from the person 168, looks into the person's eyes, looks down at the floor, at a computer screen, reaches for a tool, etc., the light(s) 124 may be deactivated—or may be dimmed, such that the amount of light is not a disturbance to the patient or others. These determination may be made using one or more computer vision, facial detection, or other detection algorithms, and may aid in extending battery life for the loupe system(s) 102.

In some non-limiting embodiments, additional cues or information may be used to activate or deactivate the light(s) 124. For example, a heat sensor(s) 180, or other sensor type, may be used to detect that the head-worn device 130 is no longer being worn by the user 160 (e.g., has been removed, is put into a non-operating position (e.g., on top of user's head, around user's neck, etc.), and/or is otherwise no longer being used. For example, the heat sensor(s) 180 may be on the nose pad of eye-glasses, on the temples along the ears of eye-glasses, inside a helmet in contact with the user's head or forehead, and/or otherwise located on the head-worn device 130 and capable of detecting changes in temperature that indicate the head-worn device 130 is no longer in operating position. In some embodiments, a threshold period of time may be used to determine when to turn on or off the light(s) 124, such as a threshold amount of time (e.g., 3 seconds, 5 seconds, 10 seconds, etc.) where the heat sensor(s) 180 indicates the head-worn device 130 is not in operating position. In addition, a microphone(s), a button (e.g., button 202 of FIG. 2A), a switch, a touch-sensitive surface, and/or another I/O device(s) 126 on the head-worn device 130, a power component 164, and/or another component of the loupe system(s) 102 may be used to turn on and/or turn off the light. For example, the user 160 may provide voice commands to a microphone(s) to turn on or off the light(s) 124 and/or to control the functionality of both photo and video (e.g., "start recording", "capture image", "stop recording", etc.), may turn on or off the light with a button or switch, may press or touch a touch-sensitive or heat-sensitive surface (e.g., on the rims or temples of eye-glasses). In addition, in some embodiments, such as where a patient's eyes may be fully or partially occluded (e.g., to protective eye-wear, head-wear, etc.), markers may be placed on or disposed on (e.g., during manufacture) a patient's protective eye-wear, head-wear, and/or the like, and the markers may be leveraged by the loupe system 102 to perform various functions—e.g., to turn on or off the light, to turn on or off the camera, etc. For example, when a user of the loupe system 102 raises his or head up towards the patient's eyes, image processing techniques, machine learning models, and/or the like may be used to identify the markers and trigger the associated operations or commands.

In addition to controlling activation or deactivation of the light(s) 124, the light(s) 124 may be controlled based on the image data and/or the IMU(s) 112. For example, one or more motors 183 may be used to maneuver or manipulate the light(s) 124 with respect to the head-worn device 130. As such, as the user 160 moves his or her head, the light(s) 124 may be adjusted to maintain light coverage within a certain region or area of the person. The manipulation of the light(s) 124 using the motor(s) 182 may be determined from the image data, such as by identifying the light in an image(s) and/or by identifying markers, guides, or features of the person in the image that may be used to determine where the light is shining. For example, intrinsic and/or extrinsic parameters of the light(s) 124 and the camera(s) 116 capturing the image data may be known, and the relative locations, positions, orientations, and/or other parameters of the light(s) 124 and the camera(s) 116 may be determined from this information. As such, a determination of how to adjust or manipulate the light(s) 124 as the user 160 moves his or her head may be determined using this information such that the light(s) 124—when physically capable of doing so—is shining at a particular region or within a threshold region. In such examples, where the light(s) 124—based on a position, orientation, or other aspect of the head-worn device 130—is unable to shine at the desire region or within the threshold region, the light may be deactivated.

Figure 1B:
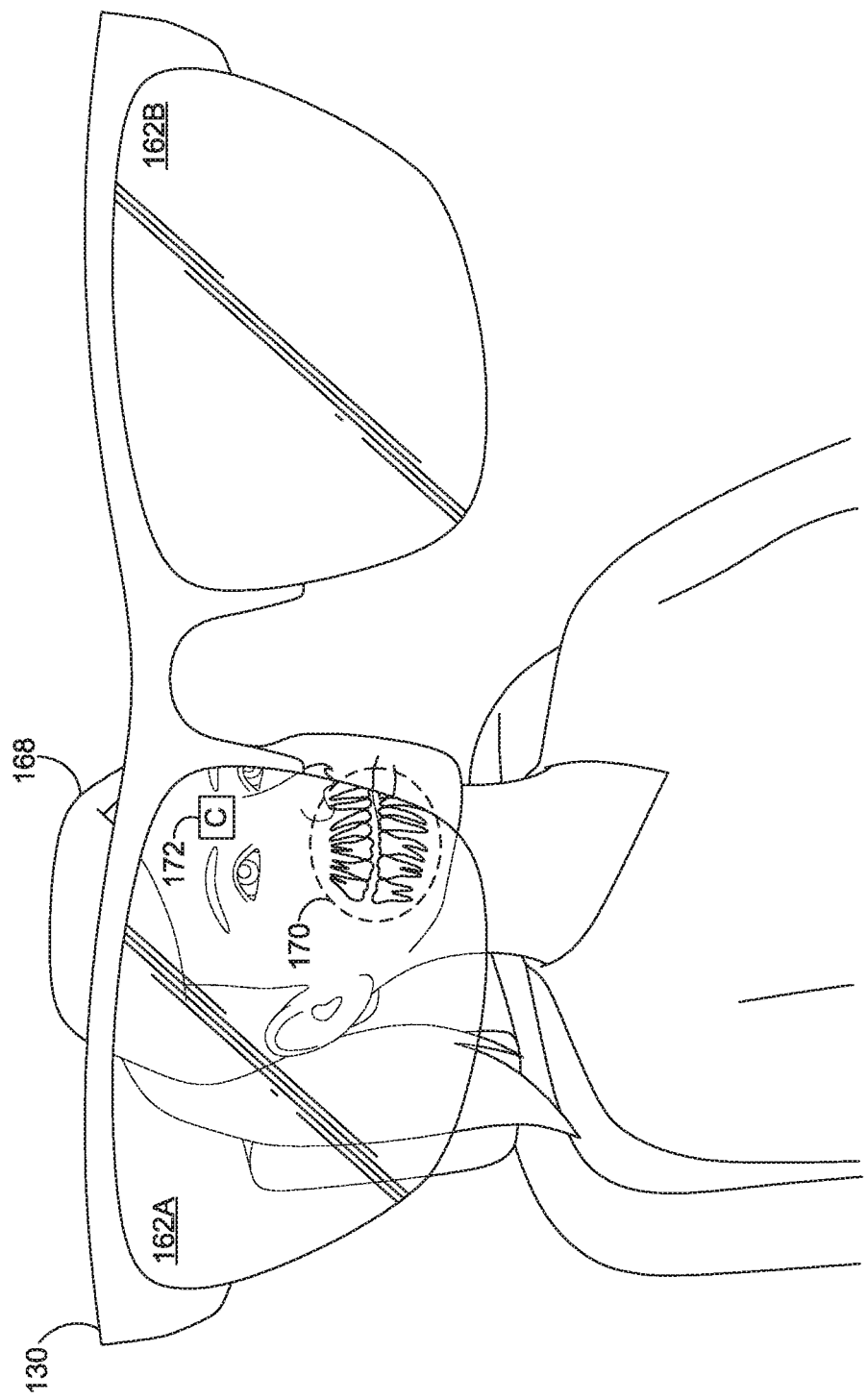
FIG. 1B is an example illustration from the perspective of a user of an AR-assisted loupe system, in accordance with some embodiments of the present disclosure.

With reference to FIG. 1B, in some embodiments, the loupe system(s) 102 may be used for augmented reality applications. For example, an AR system 120 may be implemented using the loupe system(s) 102, the local client device(s) 104, and/or the server(s) 106. As such, the processing of image data generated by the camera(s) 116, the processing of medical imaging data generated by one or more medical imaging devices, and the generating of AR-content using the image data and the medical image data may each be performed by one or more of the loupe system(s) 102, the local client device(s) 104, or the server(s) 106. Presentation of the AR-content—e.g., projection of the AR-content on a lens(es) of the head-worn device 130—may be performed by the loupe system(s) 102, and specifically by an AR projection device disposed on or otherwise associated with the head-worn device 130, in non-limiting embodiments.

As described herein, the medical imaging data may be generated by one or more imaging modality from the array of imaging modalities, such as but not limited to X-rays, computed tomography (CT), magnetic resonance imaging (MRI), ultrasounds, or nuclear imaging.

For example, although not illustrated in FIG. 1B, the head-worn device 130—which is illustrated as eye-glasses in FIG. 1B—may include at least a portion of the AR system 120 disposed thereon. The AR system 120 may include one or more projection devices or components for projecting AR-content on one or more lenses 162 (e.g., lens 162A and 162B) of the head-worn device 130. The AR-content may be generated and projected or displayed using any technique, such as but not limited to those described herein. For example, the camera(s) 116 disposed on the head-worn device 130 may be used to generate image data of the person 168 in real-time or near real-time. In some embodiments, the person 168 may have one or more markers 172 (or guides) attached thereto. Although only one marker 172 is illustrated, this is not intended to be limiting, and any number of markers may be used. For example, where computer vision triangulation (or reconstruction), two-dimensional (2D) mapping, three-dimensional (3D) mapping, or another tracking technique is used, the head-worn device 130 may include two or more cameras 116 (e.g., camera 116A, 116B and 116C as illustrated in FIG. 1A) and two or more markers 172 and/or features of the person. The "C" on the marker 172 may indicate center, and additional markers—such as "L" for left and "R" for right—may also be attached on a left side and a right side of the "C" marker 172 at some location on the person 168, respectively. As described in more detail herein, the markers 172 may be used for accurate alignment of the AR-content projection with respect to the person 168 to provide a more clear visualization of patient data (e.g., medical imaging data) related to the person 168 for the user 160 of the head-worn device 130. In addition to, or alternatively from, using the markers 172, other alignment techniques may be used. For example, features of the person 168—such as eyes, ears, nose, mouth, lips, jaw, etc.—may be used to determine positioning for projection of the AR-content.

In any embodiment, the locations of the markers 172 and/or the features of the person 168 may be determined using the image data generated by the camera(s) 116, and this information may be used to align medical imaging data with the markers 172 and/or features from the image data to generate AR-content that is to scale, as well as to project the AR-content at a location that aligns accurately with a real-world location of the feature of the person 168 virtually represented in the AR-content. For example, with respect to FIG. 1B, X-ray data may be correlated with the image data to determine AR-content 170 that includes teeth of the person 168. The scale of the AR-content 170 may be determined using one or more markers 172 and/or features of the person 168, and the location of the projection of the AR-content—e.g., overlaid on a cheek of the person 168 corresponding to an actual location of the teeth of the person behind the cheek wall—may also be determined using the markers 172, the features of a patient's face, the features and/or anatomy of the patient's oral cavity, etc. For example, because the person may have been wearing the markers 172—e.g., radiographic markers—during the generating of the medical imaging data using the medical imaging device, and may still be wearing the markers 172 during the AR projection, the alignment of the AR projection 170 with the person 168 may be accurately determined with medical precision. As a result, when the user 160 of the head-worn device 130 is performing a procedure on the person 168 that may have conventionally be a blind procedure, or at least partially blind procedure, the user 160 may be able to visualize the location of features (e.g., teeth) of the person based on the AR-content. In addition, by using this visualization technique, the degree of comfort for the person 168 may be increased.

For example, with respect to a dental procedure, the person 168 may not be forced to open their mouth as wide, or may be able to have smaller sized mouth props, because the user 160 (e.g., dentist or oral surgeon)—due to the accurate and additional visualization from the AR-content 170—may not need as much of an opening in the oral cavity to effectively perform the procedure. For an implant surgery, a determination of the depth, position, and angulation may be made, and this determination may aid the generation of the AR-content for display or projection on a lens of the head-worn device 130. For example, an indicator may be included in the AR-content such that a dentist or oral surgeon may place the implant in the ideal location. As such, the AR-content that may be generated from X-ray data and image data generated by the camera(s) 116 may be supplemented with indicators or other information to aid in performing one or more procedures. In such an example, the location, orientation, or other information of the tool being used to perform the procedure may be tracked, and thus known, and this information may be used to update the visualization to provide a visual cue that the depth has been reached. In addition to a visual cue, an audible, tactile, haptic, or other cue type may be generated. In some examples, a visual representation of at least a portion of the tool(s) being used for a procedure may be included in the AR-content and projected in the visualization. This may be useful in many procedures or surgeries, such as where the tools, components, or other devices are obscured either by skin, bone, organs, and/or other obstacles (e.g., hands or other body parts of the surgeon, the surgeon's helpers, etc.). For example, with an implant for a molar, being able to visualize the location, orientation, and depth of the drill within the visualization from the AR-content may increase accuracy, awareness, and confidence during the procedure.

Similar benefits may be realized during tooth implants, bone grafts, and/or the like. For example, during a tooth implant, tissue flap opening may be required to visualize the bone underlying the tooth to increase accuracy during the procedure. However, this procedure is not only more invasive, it also requires longer recovery periods and increases risk of infection. Some approaches use surgical guides created from molds, and then use a tissue punch to access the bone for implanting, but this technique also requires that the mold is accurately created, and leaves no room for adjustment or visualization during the actual procedure. In addition, the creating of the mold requires a first visit, and then the mold must be fitted at a subsequent visit to confirm that the mold fits. If the mold does not fit, a new one must be created, thus potentially further prolonging the already extended period for repairing what may be an uncomfortable or painful intraoral issue. However, using the systems and methods described herein may allow for visualizations of the bone structure using AR-content generated using medical imaging data, image data from the camera(s) 116, markers, features of the person, and/or other information. As such, as the dentist or oral surgeon performs a tooth implant, the location of the bone (e.g., to ensure a central-placed implant), the location of the drill, and/or the location of surrounding teeth may be included in the visualization to help guide the procedure. In some embodiments, surgical guides may still be used, or robots may be used, and the AR-content may supplement the use of the surgical guides, robots, and/or other devices. For example, using the visualization from the AR-content in addition to the surgical guide (which may also be virtually represented in the AR-content) may allow for more confident and accurate procedures. As another example, the use of a robot for a tooth implant (or another medical procedure) may be supplemented with the AR-content to help the surgeon or doctor visualize the robotic components as the procedure is taking place—thereby increasing accuracy and confidence while also preventing previously unidentifiable issues.

As another example, and with respect to bone fracture repair, markers and/or features of the person may be captured in the medical imaging data as well as the image data from the camera(s) 116, and the visualization from the AR-content created as a result may help guide positioning of screws, pins, rods, plates, and/or other repair components. This additional visualization from AR-content may allow for less invasive surgery—and less scarring—as a result of the external virtual visualization allowing for reduced internal real-world visualization (e.g., incisions or other openings of the skin may be reduced). Additionally, AR-content generated within the loupe system 102 may aid in the closure of a fracture by helping the clinician place the bones in the correct position prior to the fabrication of a cast. This may help avoid surgery in certain cases by allowing for ideal fracture reduction without surgery.

As a further example, with respect to heart stent placement, the stent may be inserted through a femoral artery in the leg and tracked up through to the heart. Using the loupe system(s) 102, described herein, an AR visualization may be generated to help the user (e.g., surgeon) track the stent as the stent—and associated components/tools—make their way up through the femoral artery. Traditionally, live X-rays or other imaging techniques are used to capture continuous images of the stent as the stent moves through the body, and the surgeon may view the live X-rays or other images to guide the stent. However, this traditional approach takes the surgeon's eyes off of the patient, requires that the surgeon use a visualization from the X-rays to guide the stent, and also greatly increases radiation exposure to the patient, surgeon, and all personnel inside the operating room. This dissociation of the surgeon's focus from the actual placement increases the complexity of the procedure, and may result in more complications. Using the system described herein, AR-content may be used to replace or supplement traditional techniques such that the surgeon may visualize the location of the stent and/or surrounding arteries and organs as the AR-content is overlaid on the patient during the procedure. For example, the AR-content may serve as "X-ray vision" for the surgeon and allow the surgeon to look at the actual location of the stent within the patient while looking at the patient—and not at a screen or other display showing X-ray images. In this example, the live X-rays may capture the person, the stent, one or more features of the person, and/or one or more markers on the person, and this information may be used in combination with image data from one or more camera(s) 116 to generate the AR-content. The AR-content may then be projected onto the lens of the head-worn device 102 such that a virtual visualization of the live X-rays is overlaid onto the person in semi-virtual space.

Figure 1C:
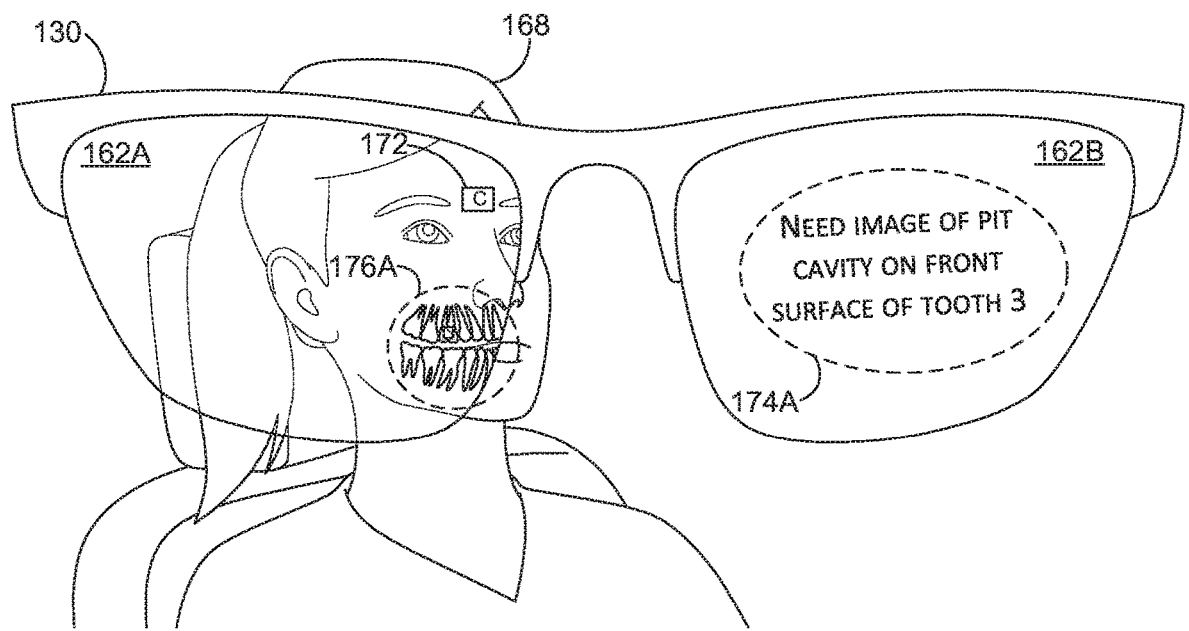
FIG. 1C is an example illustration of providing notifications of patient information to a user of an AR-assisted loupe system, in accordance with some embodiments of the present disclosure.
Figure 1C:
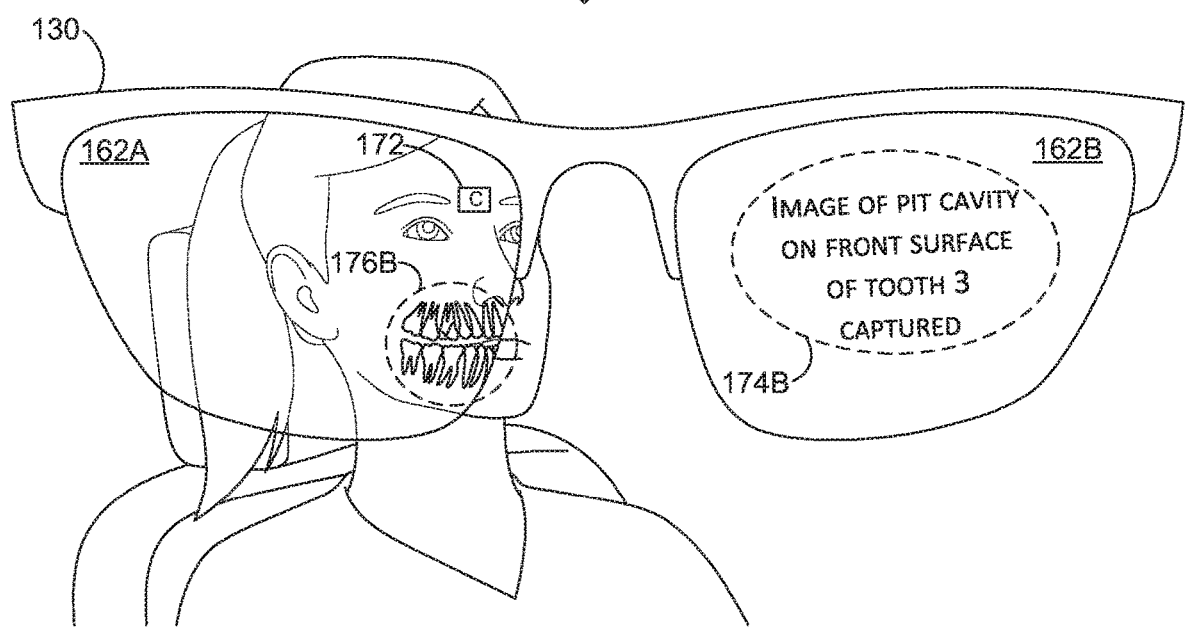

With respect to FIG. 1C, additional AR-content may be generated for display to the user of the head-worn device 130. For example, for patient records and/or for insurance purposes, images of cavities, tooth implants, missing teeth, misaligned teeth, etc. may be captured. In conventional approaches, intra-oral cameras may be used to capture this information, or an external camera may be used to capture this information. However, the capturing of this data required that the tooth to be captured was determined by a dentist or assistant, the image was captured, and the image was then analyzed by a person to determine that the tooth was actually captured. Using this technique, images are often not captured or are not clear enough to satisfy insurance standards. In addition, the use of intra-oral cameras is often unsanitary as the user of the camera must manipulate the camera within the oral cavity, which may lead to transfer of bacteria or germs to the practitioner. As such, in some embodiments of the present disclosure, AR-content (e.g., AR-content 174A, 174B, 176A, and 176B of FIG. 1C) may be generated to facilitate the accurate and complete capture of the necessary information for patient records and/or insurance purposes while also increasing compliance with sanitary standards.

For example, a medical application(s) 134 on the local client device(s) 104 may include an identifier of what information needs to be memorialized via images. This determination may be made by a person (e.g., doctor, assistant, etc.) and/or may be made by an analysis of medical imaging data and/or image data. For example, the medical application(s) 134 (and/or one or more applications on the server(s) 106) may analyze patient medical imaging data and/or image data to determine where cavities exist (e.g., by analyzing bone density information), where teeth need to be replaced, where gaps exists, where teeth are misaligned, etc., and may populate this information in the medical application(s) 134. The information may then be used to aid the user 160 of the head-worn device 130 in capturing the necessary image data while with the person 168 (e.g., a patient). Textual information may be generated within the AR-content to indicate to the user 160 what needs to be captured, adjustments that need to be made to capture a suitable image (e.g., turn to left, right, up, or down, open up mouth of patient wider, etc.), and that a suitable image was captured. The determination that a suitable image was captured may be made by the medical application(s) 134 (executing on the local client device(s) 104 and/or the server(s) 106) by analyzing the image data generated by the camera(s) 116—e.g., using a computer vision algorithm or another algorithm. The location and scale of the projection of the AR-content may be determined, similar to as described herein, using markers, guides, features of the person, and/or other supplemental information.

For example, with respect to the upper portion of FIG. 1C, the AR-content 174A may provide an indication projected on a lens(es) 162 of the head-worn device 130 reciting "Need image of pit cavity on front surface of tooth 3." In addition to the textual indication, the AR-content 176A may provide a visual indication as an overlay of X-ray data (or other medical imaging data) on the person 168 with a visual indicator on the tooth to be captured. Once it has been determined that a suitable image of the tooth has been accurately captured, the AR-content 174B may provide an indication projected on a lens(es) 162 of the head-worn device 130 reciting "Image of pit cavity on front surface of tooth 3 captured." In addition to the textual indication, the AR-content 176B may provide a visual indication as an overlay of X-ray data (or other medical imaging data) on the person 168 with a visual indicator on the tooth that the image was captured (e.g., a check mark in the example illustration of FIG. 1C). As a result of this process, each of the images that need to be captured may be presented to the user 160 without requiring the user to manually determine and confirm each of the images has been captured. This not only expedites the process of capturing the proper images, but also increases the accuracy and thoroughness of patient records as well as insurance claims. In some embodiments, the images that are captured may be uploaded and saved for access by the person 168 (e.g., the patient) via his or her remote client device(s) 108 within a client application(s) 150. For example, the person 168 may be able to access the images and insurance information, as well as other information via patient portal—as described in more detail herein.

In some non-limiting embodiments, the image data captured over time for a particular person 168 (e.g., patient) may be analyzed to track changes. For example, with respect to a dentist or orthodontist, the images captures using the camera(s) 116 may be analyzed over time to detect movement or changes in condition of teeth (e.g., presence of cavities, color changes, etc.). Not only can this information be helpful for determining a progression of the teeth (either positive or negative) over time, this information may be used to aid in generating AR-content for the user 160 (e.g., the dentist, orthodontist, oral surgeon, etc.). For example, the current location of a tooth (or teeth) may be used—in addition to one or more features of the person and/or markers or guides—to determine a location to virtually overlay a prior location of the tooth (or teeth). This way, the user 160 may visualize the movement by comparing the current location to the prior location(s) captured during prior visits as captured in the image data. In some embodiments, the movement may be analyzed by a medical application(s) 134 to determine if the movement is positive (e.g., the braces have moved the teeth toward a final, goal location) or negative (e.g., the patient's teeth have moved more out of alignment causing potential jaw or alignment issues), thereby enabling the comparison of actual movement to expected movement according to a treatment plan. This information may be memorialized for later review by the patient, the doctor, the dentist, etc., or may be used to aid in generation of AR-content. For example, an indicator may be overlaid on the tooth (or teeth) of the patient within the AR-content to indicate to the user 160 that the particular tooth (or teeth) has moved in a positive or negative direction. This information may help the user 160 in determining a proper course of action, such as to adjust braces, recommend braces, remove teeth, and/or to perform another procedure type.

Figure 1D:
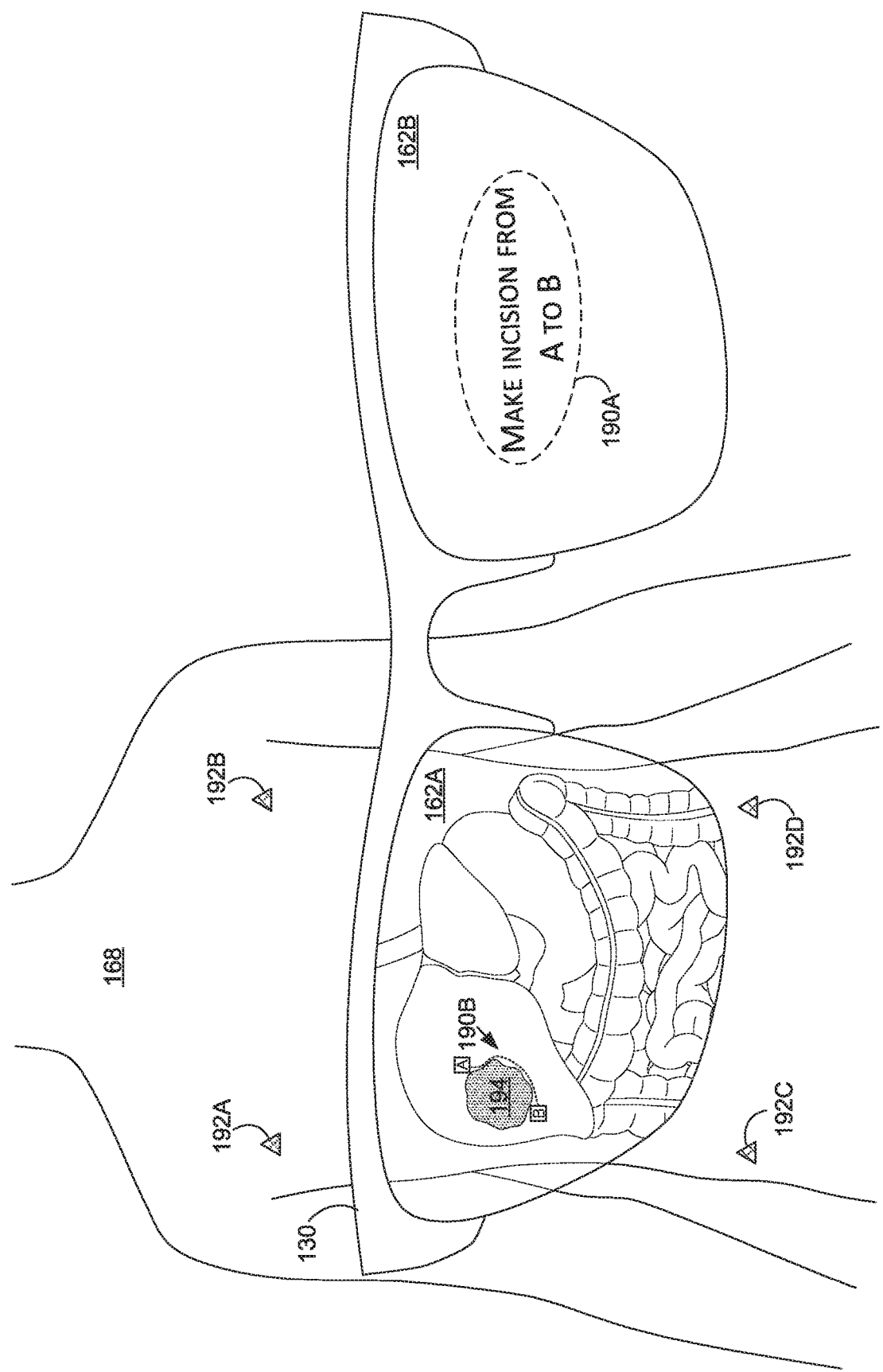
FIG. 1D is another example illustration from a perspective of a user of an AR-assisted loupe system, in accordance with some embodiments of the present disclosure.

With reference to FIG. 1D, FIG. 1D is another example illustration from a perspective of a user of an AR-assisted loupe system, in accordance with some embodiments of the present disclosure. For example, the loupe system 102 may be used to generate AR-content (e.g., AR-content 190A and 190B) to aid a user of the head-worn device 130 in performing one or more procedures. With respect to FIG. 1D, the AR-content 190 may be generated for tumor removals or visualization of tumors when examining a person 168. For example, medical imaging data may represent one or more tumors, and when extracting the tumor(s), the AR-content 190 may provide a virtual visualization of a tumor 194 and its location with respect to the person or patient. As described herein, various techniques may be used to leverage markers 192 (e.g., 192A-192D) for accurately localizing the AR-content 190 with respect to the person 168. This information may aid the surgeon in determining where to start the incision (e.g., at point "A"), as well as how large the incision should be (e.g., to end at point "B"). In some examples, the incision may be determined as part of the AR-content generation, such that a virtual representation of the incision is included in the AR-content 190B and virtually overlaid on the person or patient 168 at the location of the incision. As a result, the surgeon or user of the head-worn device 130 may create the incision by following the incision from the virtual representation in the AR-content. In some embodiments, the AR-content may help guide the surgeon through the different layers of tissue while performing a surgery. For example, the AR-content 190 may provide visual indicators corresponding to various vital structures— e.g., nerves and blood vessels—that are known to exist in each layer of tissue. As such, the loupe system 102 may track—e.g., using image processing techniques, such as those described herein—the procedure layer by layer and automatically generate AR-content 190 to aid the user. In such an example, once a first layer is cut through, a notification may appear as AR-content 190 on a lens 162 that indicates what to be on the look for (e.g., "avoid nerve X") in the next and currently visible and/or AR-content 190 indicating a known (e.g., from medical imaging data and localized via triangulation or other techniques) or estimated location of a vital structure may be generated and overlaid on the person or patient 168. This process may greatly aid in the avoidance of vital structures, e.g., nerves and blood vessels.

Additionally, this AR technology may provide the surgeon an opportunity to practice the surgery before performing on the patient. For example, by leveraging the medical images taken of the patient, AR-content may be generated for creating or simulation the unique anatomy of the patient, and the user may be able to perform the surgery on a mannequin, a human patient simulator, through visualization, and/or the like. In addition, even where the surgery is being simulated, markers—e.g., corresponding to the markers 192—may be placed on a human person simulator or other simulated object, and the AR-content may be generated accurately with localization corresponding to the actual patient. As a result, the incisions, locations of vital structures, and/or other information corresponding to the surgery or procedure may be accurately displayed even during the simulation—thereby increasing the accuracy of the simulation and leading to more comfort and precision during the actual surgery or procedure. In some embodiments, the AR technology may be used for general diagnosis and examination purposes. For example, imaging can be overlaid from a patient using AR to aid in the diagnosis process to identify or rule out abnormal vs. normal findings.

Figure 1E:
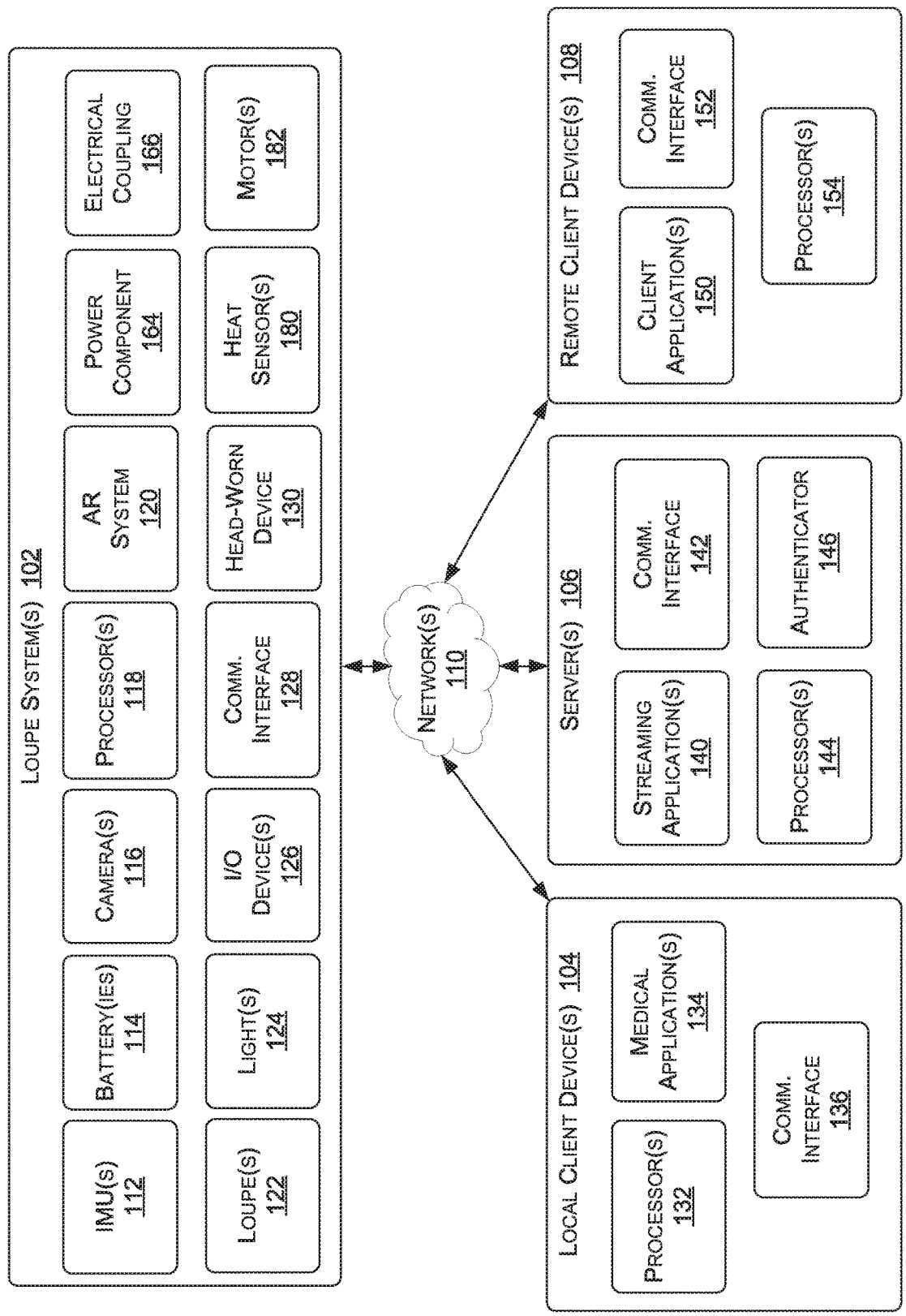
FIG. 1E is a block diagram of an example loupe system for lighting control, streaming, and augmented reality (AR) assisted procedures, in accordance with some embodiments of the present disclosure.

With respect to FIG. 1E, in some embodiments, one or more loupe(s) 122 may be used by the user 160 of the head-worn device 130. The loupe(s) 122 may have any magnification depending on the preferences of the user 160 and/or the type of procedure being performed. For example, the loupe(s) 122 may have a magnification of 2.5×, 3.5×, 4×, 4.5×, etc. In some examples, the image data captured by the camera(s) 116 may be captured at a zoom or aspect ratio that mimics the magnification of the loupe(s) 122—whether or not the loupe(s) 122 are actually used (e.g., where loupe(s) 122 aren't used, the image data may still be generated with a field of view that mimics the use of loupe(s) 122). For example, when capturing image data of a medical procedure for streaming and/or later viewing, the viewer (e.g., a student, physician, interested party, etc.) may desire to view the procedure from the viewpoint of the user 160 of the head-worn device 130. As such, the zoom of the camera(s) 116 may be adjusted such that the field of view captured in the image data is similar to the field of view of the user 160 through the loupe(s) 122. In some embodiments, the zoom may be optical zoom, while in others, the zoom may be digital zoom. In addition, in some examples, the image quality or aspect ratio may be such that cropping the images may result in a field of view that mimics the field of view of the user 160 through the loupe(s) 122 without any digital or optical zoom. For example, where 4K image data is generated, the images may be cropped to 1080p quality at an aspect ratio or field of view that mimics that created by the loupe(s) 122. In such examples, any number of different crops may be made to adjust the field of view to mimic views of loupe(s) 122 of varying magnifications. For example, a first user may wish to view the image data (e.g., video of a procedure) at a first magnification mimicking 2.5× loupe(s) 122, while a second user may wish to view the image data at a second magnification mimicking 3.5× loupe(s) 122. As such, different crops may be generated to accommodate both users. In other examples, such as where two or more cameras 116 are used, different cameras 116 may capture image data at varying zooms, aspect ratios, and/or qualities to provide different fields of view, magnifications, and/or other parameters for viewing by users.

The I/O device(s) 126 may include a microphone(s), a speakers(s), a touch surface(s), a button(s), a switch(es), and/or other device types. For example, the microphone(s) may be used to provide voice commands, to generate recordings for transcriptions or later review, to provide commentary during surgery, to capture commentary during procedures for listening while viewing the images and/or video generated by the camera(s) 116, etc. Where voice commands are used, the voice commands may be used to activate the camera(s) 116, deactivate the camera(s) 116, start a recording, pause a recording, resume a recording, activate the light(s) 124, deactivate the light(s) 124, and/or other perform other operations or tasks. The speaker(s) may be used to provide feedback to the user 160, such as to capture certain images, to make certain adjustments, etc.

The power component 164 may include one or more of the battery(ies) 114, one or more components of the AR system 120, the processor(s) 118, the microphone(s), the speaker(s), the button(s), the switches(s), other I/O device(s) 126, or the communication interface 128. In some embodiments, the head-worn device 130 may include one or more of the IMU(s) 112, camera(s) 116, light(s) 124, loupe(s) 122, one or more components of the AR system 120, the processor(s) 118, the microphone(s), the speaker(s), the button(s), the switches(s), other I/O device(s) 126, the motor(s) 182, the heat sensor(s) 180, the battery(ies) 114, or the communication interface 128.

The electrical coupling 166 may electrically couple the head-worn device 130 to the power component 164. The electrical coupling may include a hard-wired connection via one or more electrical cables. In some embodiments, the electrical coupling may include ribbon wire that may be capable of efficiently transporting or transmitting image data, audio data, AR data, and/or electrical power (e.g., from the battery(ies) 114 to one or more components of the head-worn device 130). Although the electrical coupling is illustrated herein, in some embodiments, the head-worn device 130 may communicate data wirelessly to the power component 164, and/or the power component 164 may not be implemented. In such examples, the head-worn device 130 may include a battery(ies) 114 disposed thereon for powering one or more components. For example, the head-worn device 130 may generate audio, image, and/or other data types, and may transmit the data to the power component 164 (where present), the local client device(s) 104, and/or the server(s) 106. For example, a housing may be disposed on the head-worn device 130 that may include a battery(ies) 114 and/or one or more components of the head-worn device 130—such as the camera(s) 116, light(s) 124, etc. In some embodiments, the power component 164 may, receive wirelessly and/or via a wired connection, the audio, image, and/or other data from the head-worn device, process the data (e.g., analyze, compress, encode, etc.), and transmit the data to the local client device(s) 104 and/or the server(s) 106.

The remote client device(s) 108 may include one or more client application(s) 150 for accessing, replaying, or storing image data, audio data, medical imaging data, and/or other data from one or more procedures and/or from patient data (e.g., via a patient portal). For example, in some embodiments, the server(s) 106 may stream or otherwise transmit (e.g., for storage) image data, audio data, and/or other data to the remote client device(s) 108 via streaming application(s) 140. In such examples, prior to sending any patient data that may be protected under medical rules and regulation, such as the Health Insurance Portability and Accountability Act (HIPAA), an authenticator 146 may authenticate the remote client device(s) 108—or the user thereof. For example, credential of the user within the client application(s) 150 may be verified, a token may be required, and/or other authentication processes may be implemented. In some examples, the users of the remote client device(s) 108 may be students, patients, doctors, and/or other types of persons, and the authentication steps may vary depending on the type of user in order to comply with medical rules and regulations. The client application(s) 150 are described in more detail herein at least with respect to FIGS. 3A-3G. Processes or operations of the client application(s) 150 may be executed by the processor(s) 154.

In some non-limiting embodiments, the loupe system(s) 102 may include a processor(s) 118 and/or one or more applications or instructions thereon for performing the analysis to determine the presence of the person and/or a feature(s) thereof, to determine and/or project AR-content, and/or to perform any other processes or operations described herein. The processor(s) 118 may be a component of the head-worn device 130, the power component 164, or a combination thereof. As such, the processing of the computer vision, facial recognition, and/or other detection algorithms may be executed by a processor(s) 118 of the head-worn device 130, the power component 164, or a combination thereof.

In other embodiments, a local client device(s) 104 may include one or more applications (e.g., medical application(s) 134) or instructions thereon for performing the analysis to determine the presence of the person and/or a feature(s) thereof, to determine and/or generate AR-content, and/or to perform any other processes or operations described herein. For example, one or more processors 132 of the local client device(s) 104 may receive the image data from the loupe system(s) 102, analyze the image data using a computer vision, facial recognition, and/or other detection algorithm, and determine whether or not a person 168 or a feature thereof is present. Once a determination is made that a person 168—or a feature thereof—is present, a signal may be generated by the local client device(s) 104 and transmitted to the loupe system(s) 102 (e.g., to the power component 164 and/or a component of the head-worn device 130) to cause the light(s) 124 to be activated. Similarly, for AR-content generation, the local client device(s) 104 may receive the image data, medical imaging data, and/or other data types that may be used to generate and/or render the AR-content.

In still further embodiments, the server(s) 106 may include one or more applications (e.g., medical application(s) 134, streaming application(s) 140, etc.) or instructions thereon for performing the analysis to determine the presence of the person and/or a feature(s) thereof, to determine and/or generate AR-content, and/or to perform any other processes or operations described herein. For example, one or more processors 144 of the server(s) 106 may receive the image data from the loupe system(s) 102 and/or the local client device(s) 104, analyze the image data using a computer vision, facial recognition, and/or other detection algorithm, and determine whether or not a person 168 or a feature thereof is present. Once a determination is made that a person 168—or a feature thereof—is present, a signal may be generated by the server(s) 106 and transmitted to the loupe system(s) 102 (e.g., to the power component 164 and/or a component of the head-worn device 130), via the local client device(s) 104, in embodiments, to cause the light(s) 124 to be activated. Similarly, for AR-content generation, the server(s) 106 may receive the image data, medical imaging data, and/or other data types that may be used to generate and/or render the AR-content.

In some embodiments, the server(s) 106 may render the AR-content in a cloud environment, capture the rendering in display or projection data, and transmit the display or projection data to the loupe system(s) 102 (e.g., via the local client device(s) 104) for display or projection as AR-content. As such, the analysis, generation, and rendering of the AR-content may be performed by the server(s) 106—thereby reducing the computation expense of the loupe system(s) 102 and/or the local client device(s) 104—and the loupe system(s) 102 may display the already rendered and captured display data. Using this approach, the computation resources and efficiency of a cloud-based platform—which may include a cloud-based GPU infrastructure—may be leveraged to generate higher quality display data for the AR system 120 with lower latency, and without requiring the local client device(s) 104 to include sufficient storage space and/or processing power.

The image data, AR-content, audio data, and/or other data types may be communicated between the loupe system(s) 102 and the local client device(s) 104 using a communication interface 128 of the loupe system(s) 102 and a communication interface 136 of the local client device(s) 104. Similarly, signals indicative of activation or deactivation of the light may be transmitted between the local client device(s) 104 and the loupe system(s) 102 via the respective communication interfaces. For example, the loupe system(s) 102 and the local client device(s) 104 may communicate over one or more networks 110, such as a local area network (LAN), a wide-area network (WAN), an ultra-low power network (ULP), a low-power network, a short range network, a low power wide-area network (LPWAN), and/or another network type. In some examples, the loupe system(s) 102 and the client device(s) 104 may communicate over one or more of Bluetooth, Bluetooth Low Energy (BLE), Wi-Fi, ZigBee, WiMax, EnOcean, Eddystone, adaptive network topology (ANT), near-field communication (NFC), IEEE 802.15, ISA100.11a, DigiMesh, WirelessHART, Ethernet, cellular (e.g., 2G, 3G, 4G, LTE, 5G, etc.), LoRaWAN, NB-IoT, SigFox, Weightless, Z-wave, and/or another communication protocol(s).

Similarly, in some embodiments, the image data, AR-content, audio data, and/or other data types may be communicated between the loupe system(s) 102, the local client device(s) 104, and/or server(s) 106 using a communication interface 128 of the loupe system(s) 102, a communication interface 136 of the local client device(s) 104, and/or a communication interface 142 of the server(s) 106. As a non-limiting example, image data may be generated by the loupe system(s) 102, transmitted to a local client device(s) 104, and the local client device(s) 104 may transmit the image data to the server(s) 106 for analysis. Similarly, the determinations, or signals representative thereof, that the light(s) 124 should be turned on or off may be communicated to the loupe system(s) 102 by the server(s) 106 (via the local client device(s) 104, in embodiments). For example, the loupe system(s) 102 and the local client device(s) 104 may communicate over one or more networks 110, such as those described herein, and the loupe system(s) 102 and/or the client device(s) 104 may communicate with the server(s) 106 over one or more of a local area network (LAN) (e.g., Wi-Fi, Ethernet, etc.), a wide-area network (WAN) (e.g., the Internet, a public switched telephone network PSTN), etc.), an ultra-low power network (ULP), a low-power network, a short range network, a low power wide-area network (LP-WAN), and/or another network type. As such, the image data, the activation signals, the deactivation signals, and/or other communications may be transmitted between and among the loupe system(s) 102, the local client device(s) 104, and/or the server(s) 106.

Similarly, the server(s) 106, the loupe system(s) 102, and/or the local client device(s) 104 may similarly communicate with the remote client device(s) 108 over the network(s) 110—including but not limited to those described herein—via communication interface 152 of the remote client device(s) 108. The local client device(s) 104 may, without limitation, be co-located with the loupe system(s) 102 such that a LAN may be used, or a direct wired connection may be used to transmit data between and among the devices. The remote client device(s) 108 may be at a remote location with respect to the loupe system(s) 102, the local client device(s) 104, and/or the server(s) 106. For an example, the loupe system(s) 102 and the local client device(s) 104 may be located at a medical facility, the server(s) 106 may be located at the medical facility and/or at a remote cloud-based facility, and the remote client device(s) 108 may be located with one or more users at any location—such as a home of the user, an educational environment, etc.

Figure 2A:
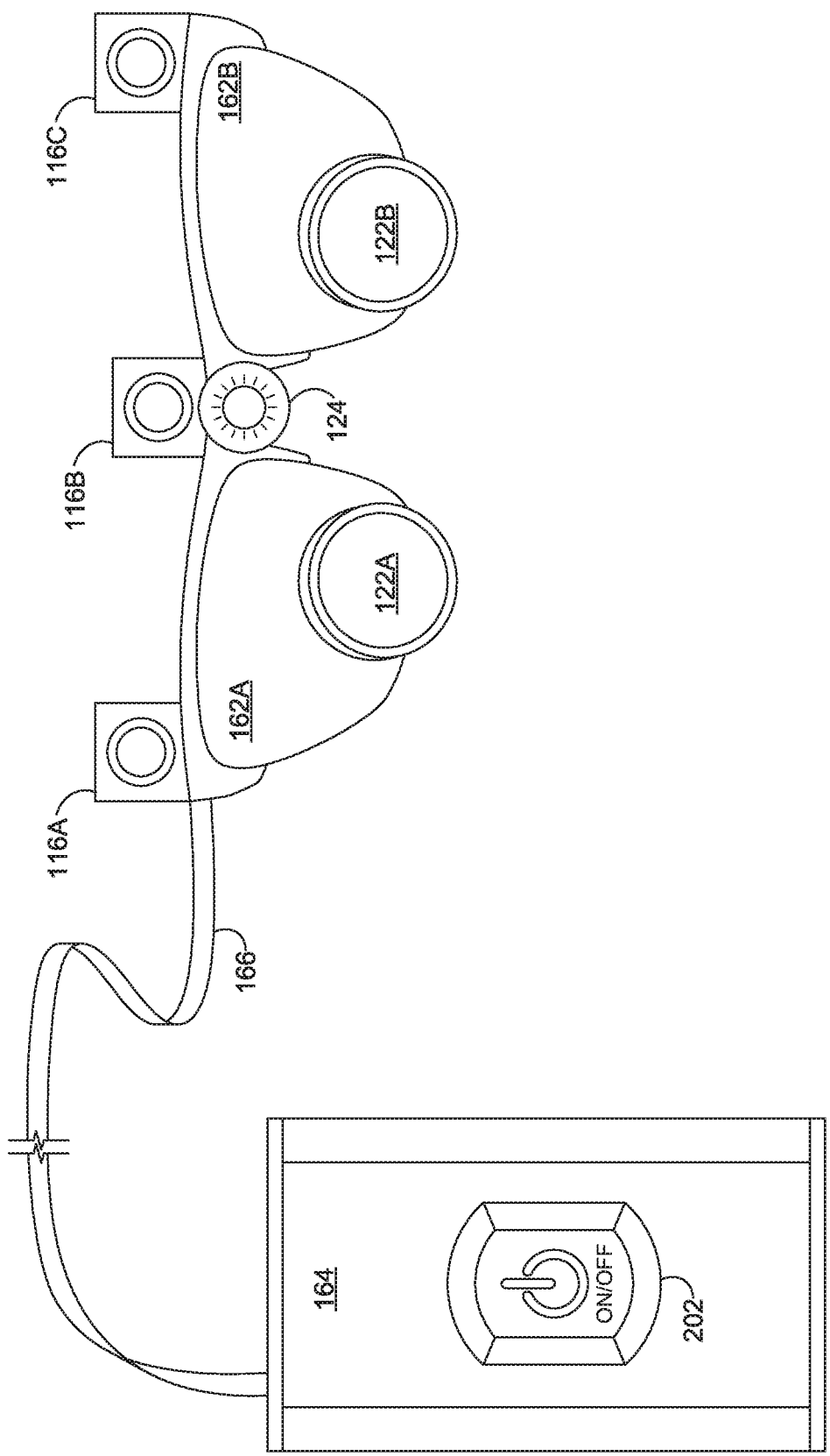
FIG. 2A is an example illustration of eye-glasses electrically coupled to a power component in a loupe system, in accordance with some embodiments of the present disclosure.

Now referring to FIG. 2A, FIG. 2A is an example illustration of eye-glasses electrically coupled to a power component in a loupe system, in accordance with some embodiments of the present disclosure. The eye-glasses represent one possible embodiment of the head-worn device 130 in the loupe system(s) 102 described herein. FIG. 2A provides another example illustration of the loupe system(s) 102 from a different perspective for illustrative purposes only. In some embodiments, the camera(s) 116 may be positioned as illustrated in FIG. 2A, while in other embodiments, the camera(s) 116 may be positioned differently. For example, the camera(s) 116 may all be in a single housing centrally positioned—or otherwise positioned—on the head-worn device 130. Each camera 116, where two or more are present, may include a different field of view, a different type (e.g., wide view, stereo, 360 degree, etc.), a different location and/or orientation, a different aspect ratio, a different image quality, and/or other different parameters.

Now referring to FIG. 2B, FIG. 2B is an example illustration of a housing associated with a head-worn device within a loupe system, in accordance with some embodiments of the present disclosure. The housing may include a camera housing, such as a housing for two or more cameras 116 (e.g., 4K cameras 116D and first-person view (FPV) camera 116E). Additional components of the housing may include a mode LED 260 to indicate a current operating mode (e.g., on/off, recording, not recording, charged, low-battery, etc.), an antenna 258 for receiving and transmitting, a battery connector 256 for connecting power to components of the device, a ground 254, a 5-12 V connection 252, a ground 250, video 248, menu 246, ground 244, a 5-12 V connection 242, a ground 240, video 238, menu 236, ground 234, receiver 232 for receiving data, transmitter 230 for transmitting data, a heat sink 228 for dispersing heat from components of the device, a Wi-Fi/recode button 226 for connecting to other devices (e.g., the local client device(s) 104), a power/mode button 224 for turning the device on/off, a Wi-Fi LED 220 to indicate a Wi-Fi connection (or other type of connection) is established or active, and a memory card 222 (e.g., a TransFlash (TF) card, a micro SD card, etc.) for storing data that is received (e.g., AR-content, audio data, etc.) and/or transmitted (e.g., audio data, image data, input data, state data, etc.).

Now referring to FIGS. 3A-3G, FIGS. 3A-3G are example illustrations of graphical user interfaces (GUIs) for streaming or viewing medical procedures and/or viewing patient information within one or more applications, in accordance with some embodiments of the present disclosure. The one or more applications may include the client application(s) 150 of the remote client device(s) 108 of FIG. 1E, and the streams of data and/or access to stored data may be received and/or accessed via the streaming application(s) 140 on the server(s) 106—e.g., after authentication by the authenticator 146. The client application(s) 150 may be used to view videos, images, and/or other recordings of procedures, surgeries, and/or the like, that are generated using the loupe system(s) 102. For example, as a user 160 (e.g., doctor, dentist, surgeon, nurse, etc.) of the loupe system(s) 102 performs an operation, procedure, general exam, etc., the user 160 may desire to record, store, and/or stream the recording of the procedure for viewing by one or more users on a remote client device(s) 108 (e.g., a laptop, computer, tablet, phone, etc.). This information may be used for educational purposes, in some embodiments. As described herein, the recordings may be generated by the one or more camera(s) 116 at one or more fields of view, magnifications or zooms, aspect rations, etc., such that one or more perspectives of the operation, procedure, etc. are available for viewing. In some embodiments, the client application(s) 150 may include a patient portal for patients to access medical information, such as recordings of procedures, medical imaging data, insurance information, images of cavities, tooth replacements, etc., and/or other information about the patient for their own use or safekeeping. In any example, the GUI(s) described with respect to FIGS. 3A-3G may include varying examples for streaming recordings, viewing stored recordings (e.g., on the remote client device(s), on the server(s) 106, etc.), searching for recordings or live-streams, changing settings, viewing patient information, viewing medical imaging data, etc.

Figure 3A:
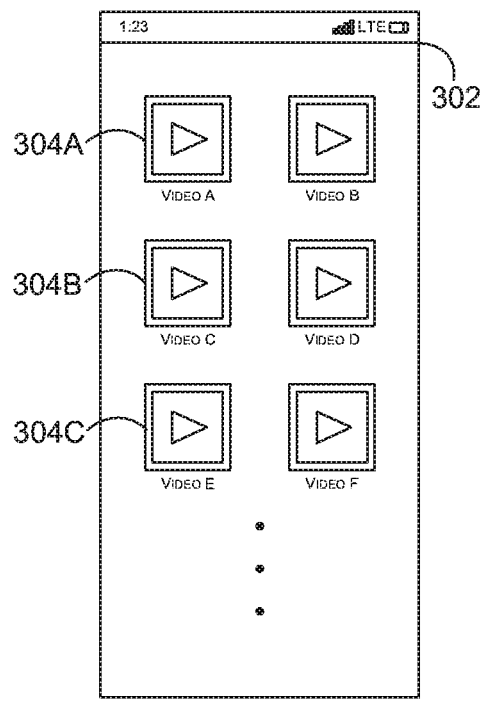
FIGS. 3A-3G are example illustrations of graphical user interfaces (GUIs) for streaming or viewing medical procedures and/or viewing patient information within one or more applications, in accordance with some embodiments of the present disclosure.
Figure 3B:
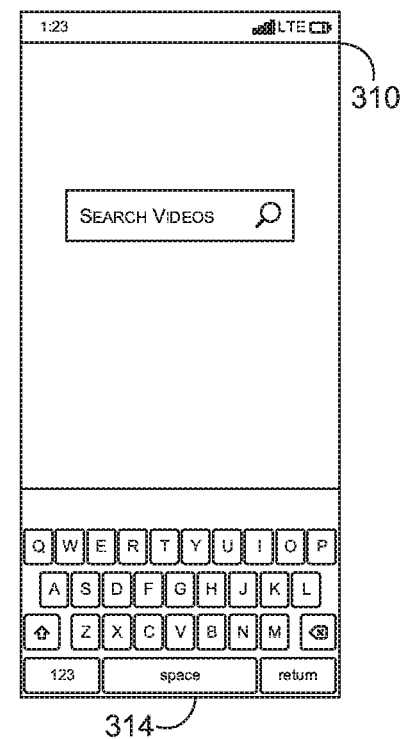
Figure 3C:
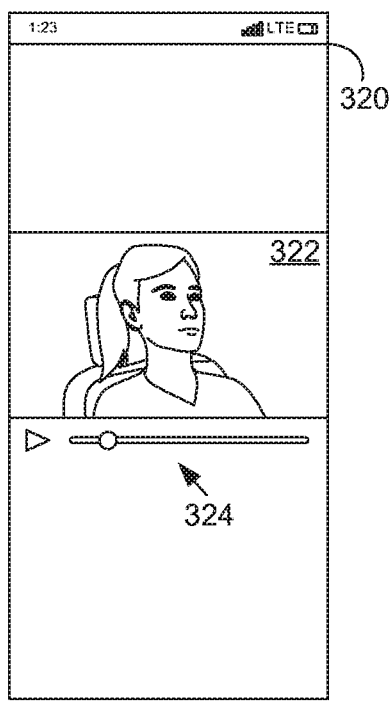
Figure 3D:
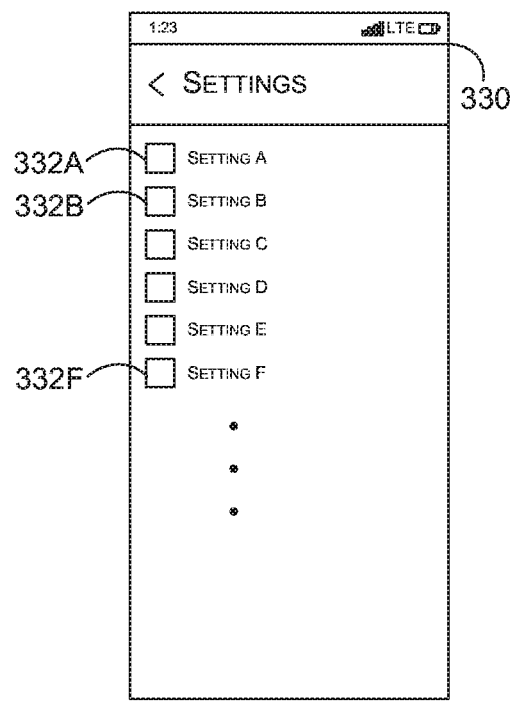
Figures 3E, 3F:
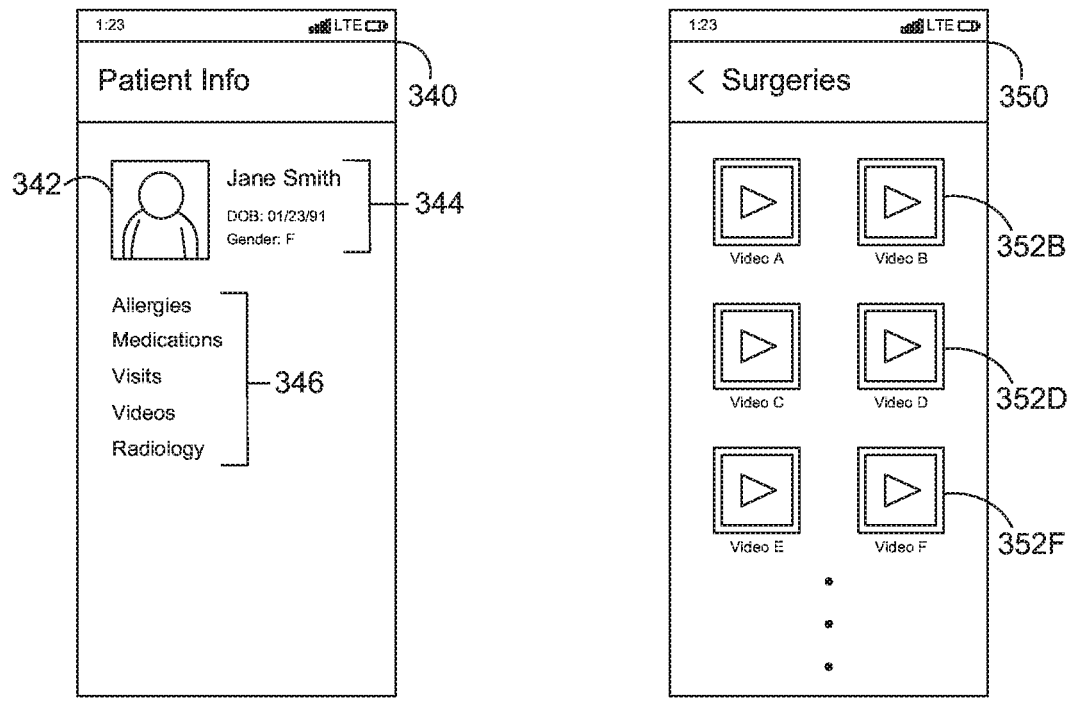
Figure 3G:
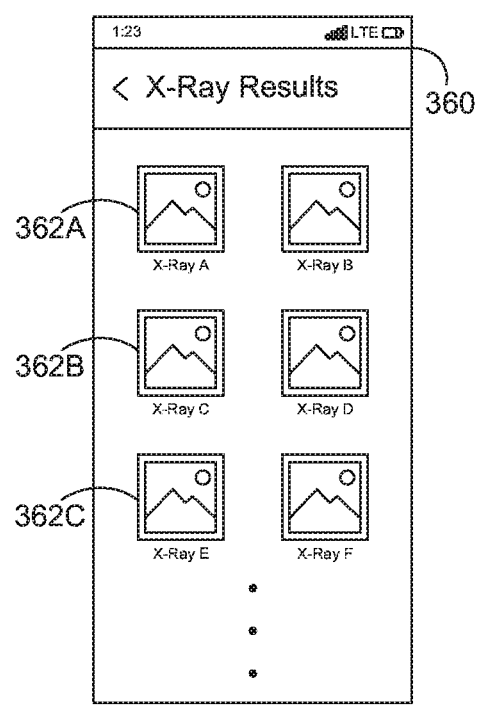

FIG. 3A includes a GUI 302 for viewing pre-recorded or live-streamed videos. For example, the user of the remote client device(s) 108 may have searched for certain video of certain procedure types, surgery types, etc., within GUI 310, and received the list of videos 304 (e.g. including videos 304A, 304B, and 304C). FIG. 3B includes the GUI 310 for searching for videos, procedures, doctors or other practitioners, etc. For example, a user may enter a search into search bar 312 using digital keypad 314 to retrieve current live streams, future live streams, pre-recorded videos, etc. In any example, the user may desire to save the videos or other data—where authorized—and may do so on his or her remote client device(s) 108. Once a video 322 or other recording type is selected, GUI 320 may playback the video 322. One or more control elements 324 may be available within the GUI 320 for controlling the playback (e.g., play, stop, pause, record, fast-forward, rewind, capture screenshot, add notes, add comments, provide commentary, etc.). The client application(s) 150 may include various settings 332, and GUI 330 may allow the user to adjust settings 332 (e.g., settings 332A, 332B, and 332F). For example, the user may be able to adjust the image quality, frame rate, other image or video settings, zoom level, magnification level, video types, login information, account type, audio settings, credential or authentication information, and/or the like.

GUI 340 may represent a GUI of a patient portal where a patient or user may access health information. For example, an image 342 of the patient, patient personal information 344, and/or patient medical information 346 may be accessible and/or editable within the GUI 340. The GUI 350 may allow the patient to access videos 350 (e.g., videos 352B, 352D, and 352F) of surgeries that were performed on them, that were performed on others, that are similar to the surgery they may be undergoing, that have been performed by their doctor, etc. Similarly, GUI 360 may allow the patient to access medical imaging data 362 (e.g., medical imaging data 362A, 362B, and 362C). In addition, as described herein, the GUI(s) may be accessed to view insurance information, images taken of cavities, etc., and/or to access other patient information—such as results of tests, etc.

Figure 4:
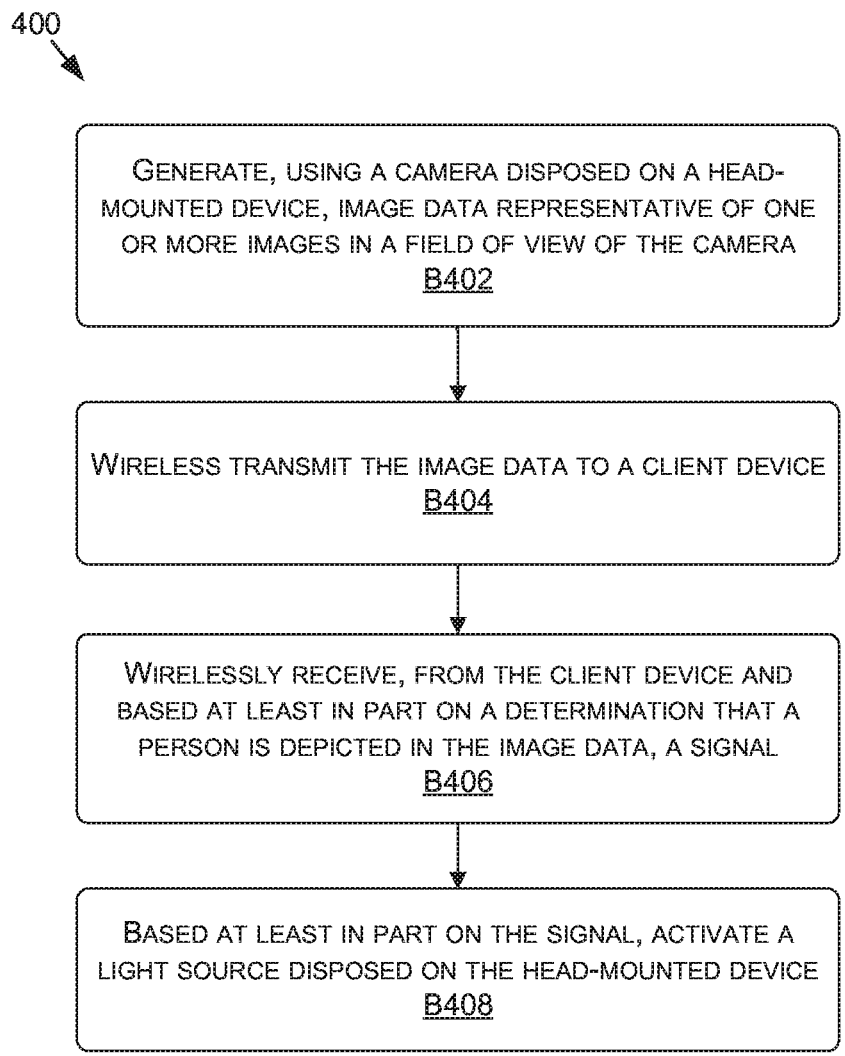
FIG. 4 is a flow diagram for an example method of using facial recognition to activate or deactivate a light source of eye-glasses in a loupe system, in accordance with some embodiments of the present disclosure.
Figure 5:
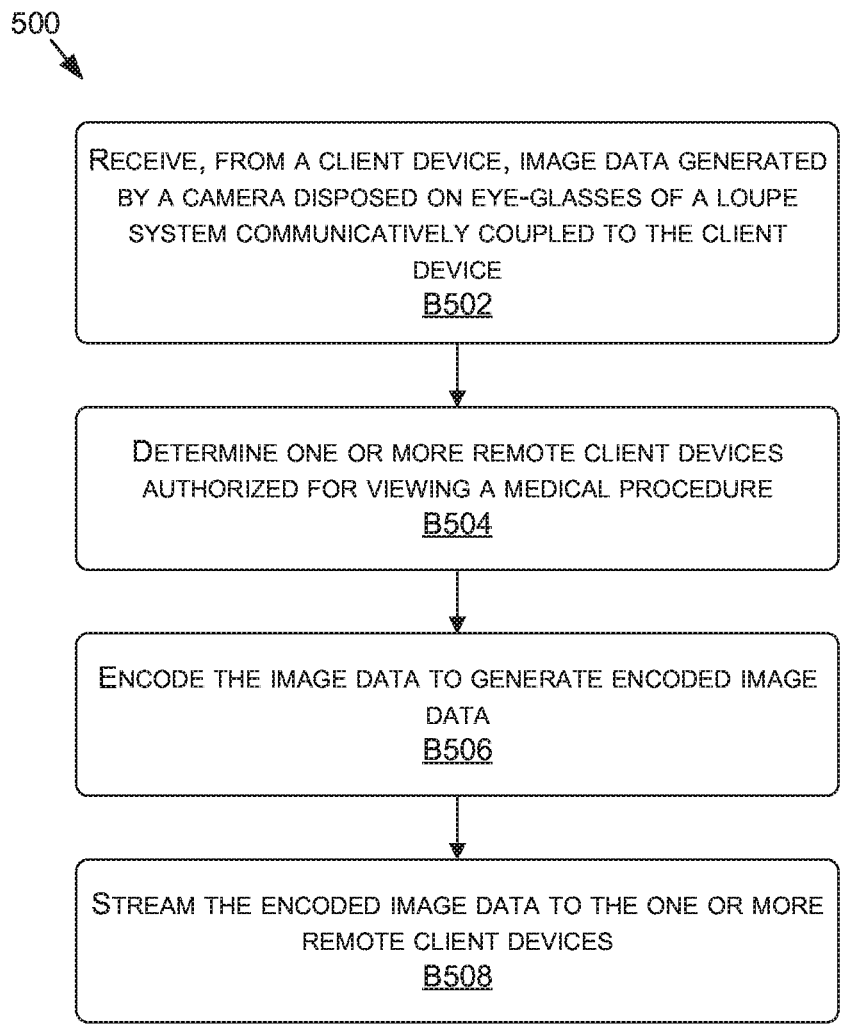
FIG. 5 is a flow diagram for an example method of streaming a medical procedure captured using a head-mounted camera to one or more remote client devices, in accordance with some embodiments of the present disclosure.
Figure 6:
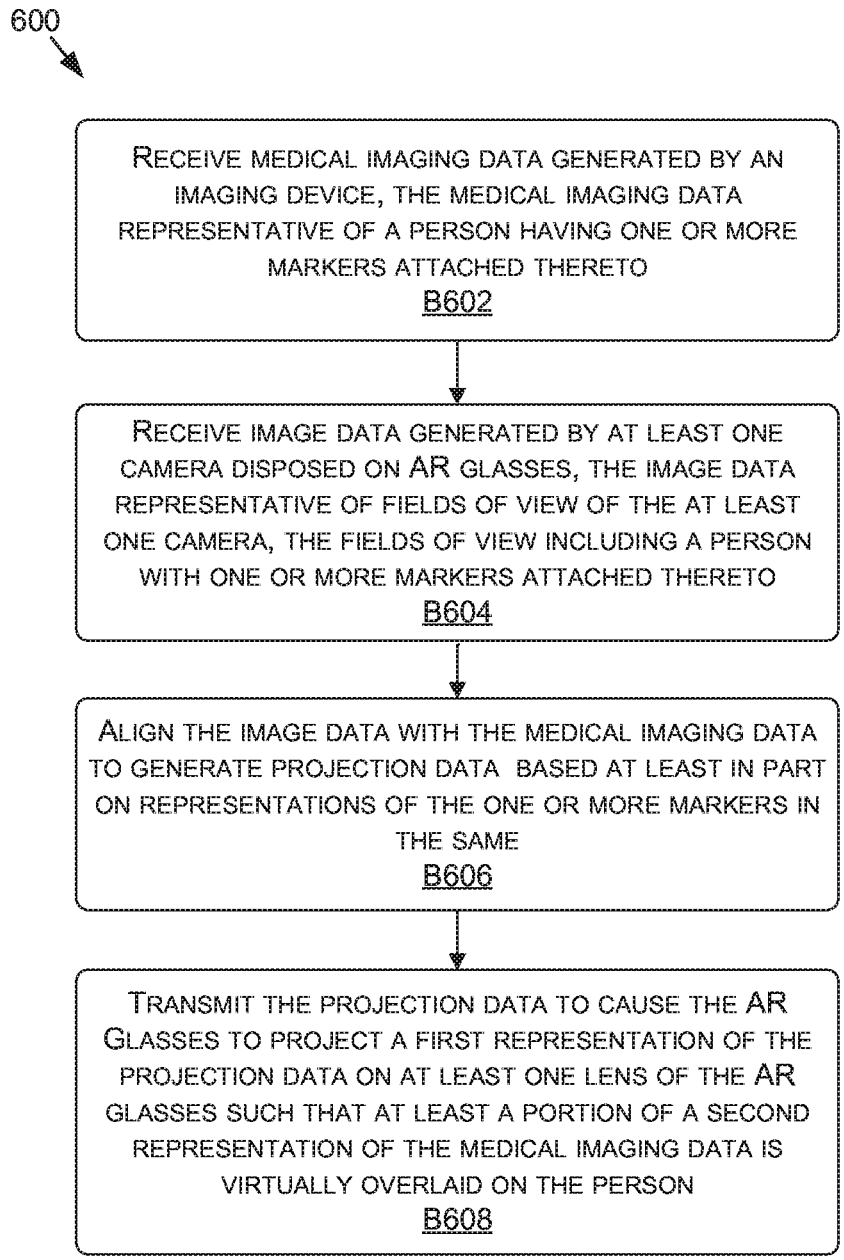
FIG. 6 is a flow diagram for an example method of using AR functionality to provide virtual visualizations to assist in medical procedures, in accordance with some embodiments of the present disclosure.

Now referring to FIGS. 4-6, each block of methods 400, 500, and 600, described herein, comprises a computing process that may be performed using any combination of hardware, firmware, and/or software. For instance, various functions may be carried out by a processor executing instructions stored in memory. The methods may also be embodied as computer-usable instructions stored on computer storage media. The methods may be provided by a standalone application, a service or hosted service (standalone or in combination with another hosted service), or a plug-in to another product, to name a few. In addition, methods 400, 500, and 600 are described, by way of example, with respect to the loupe system(s) 102 of FIGS. 1A-1E. However, these methods may additionally or alternatively be executed by any one system, or any combination of systems, including, but not limited to, those described herein.

Now referring to FIG. 4, FIG. 4 is a flow diagram for an example method 400 of using facial recognition to activate or deactivate a light source of eye-glasses in a loupe system, in accordance with some embodiments of the present disclosure. The method 400, at block B402, includes generating, using a camera disposed on a head-mounted device, image data representative of one or more images in a field of view of the camera. For example, the camera(s) 116 may generate image data representative of a field(s) of view of the camera(s) 116.

The method 400, at block B404, includes wirelessly transmitting the image data to a client device. For example, the image data may be wirelessly transmitted to the local client device(s) 104 over one or more networks 110.

The method 400, at block B406, includes wirelessly receiving, from the client device and based at least in part on a determination that a person is depicted in the image data, a signal. For example, the local client device(s) 104 may analyze the image data using one or more facial recognition, computer vision, and/or other detection algorithms to determine whether a person—or a face or other feature thereof—is depicted in the image data. Once a determination is made that a person is present, a signal may be transmitted to the loupe system(s) 102—such as the head-worn device 130, via the power component 164, in embodiments—that is representative of an activation request for activating the light(s) 124.

The method 400, at block B408, includes, based at least in part on the signal, activating a light source disposed on the head-mounted device. For example, the signal may cause the light(s) 124 to be activated.

Now referring to FIG. 5, FIG. 5 is a flow diagram for an example method 500 of streaming a medical procedure captured using a head-mounted camera to one or more remote client devices, in accordance with some embodiments of the present disclosure. The method 500, at block B502, includes receiving, from a client device, image data generated by a camera disposed on eye-glasses of a loupe system communicatively coupled to the client device. For example, the server(s) 106 may receive, from the local client device(s) 104, image data generated by a camera(s) 116 of the loupe system(s) 102.

The method 500, at block B504, includes determining one or more remote client devices authorized for viewing a medical procedure. For example, the authenticator 146 of the server(s) 106 may determine which of the remote client device(s) 108 are authorized for viewing—either via a live stream, a pre-recorded stream, or as downloadable content—the medical procedure.

The method 500, at block B506, includes encoding the image data to generate encoded image data. For example, the image data may be encoded into a format for streaming to the remote client device(s) 108, such as into a inter frame only format (e.g., P-frame only), or another suitable format for streaming.

The method 500, at block B508, includes streaming the encoded image data to the one or more remote client devices. For example, the image data, after encoding and/or compression, may be streamed to one or more of the remote client device(s) 108 for viewing, storage, or otherwise.

Now referring to FIG. 6, FIG. 6 is a flow diagram for an example method 600 of using AR functionality to provide virtual visualizations to assist in medical procedures, in accordance with some embodiments of the present disclosure. The method 600, at block B602, includes receiving medical imaging data generated by an imaging device, the medical imaging data representative of a person having one or more markers attached thereto. For example, medical imaging data may be received, where the medical imaging data was generated by one or more medical imaging devices and of a person 168 having one or more markers 172 attached thereto. In other examples, in addition to or alternatively from markers 172, one or more features of the person may be represented in the medical imaging data—such as joints, eyes, ears, etc.

The method 600, at block B604, includes receiving image data generated by at least one camera disposed on AR glasses, the image data representative of fields of view of the at least one camera, the fields of view including a person with one or more markers attached thereto. For example, image data may be received from the camera(s) 116 of the loupe system(s) 102, where the image data is representative of the person 168 having one or more markers 172 attached thereto (and/or representative of one or more features of the person 168).

The method 600, at block B606, includes aligning the image data with the medical imaging data to generate projection data based at least in part on representations of the one or more markers in the same. For example, the image data and the medical imaging data may be aligned—e.g., using the marker(s) 172 and/or features of the person 168—such that AR-content may be generated for projection at a particular location in the environment and at an accurate scale. In some embodiments, triangulation, 2D mapping, 3D mapping, or other techniques may be used to determine the alignment of the image data and the medical imaging data for generating the visualizations within the AR-content.

The method 600, at block B608, includes transmitting the projection data to cause the AR glasses to project a first representation of the projection data on at least one lens of the AR glasses such that at least a portion of a second representation of the medical imaging data is virtually overlaid on the person. For example, the projection data may be transmitted to the loupe system(s) 102—e.g., to the AR system 120 of the head-worn device 130—to cause the loupe system(s) 102 to project the AR-content onto the lens(es) of the head-worn device 130 such that a representation of the medical imaging data is virtually overlaid in AR on the person 168.

Example Computing Device

Figure 7:
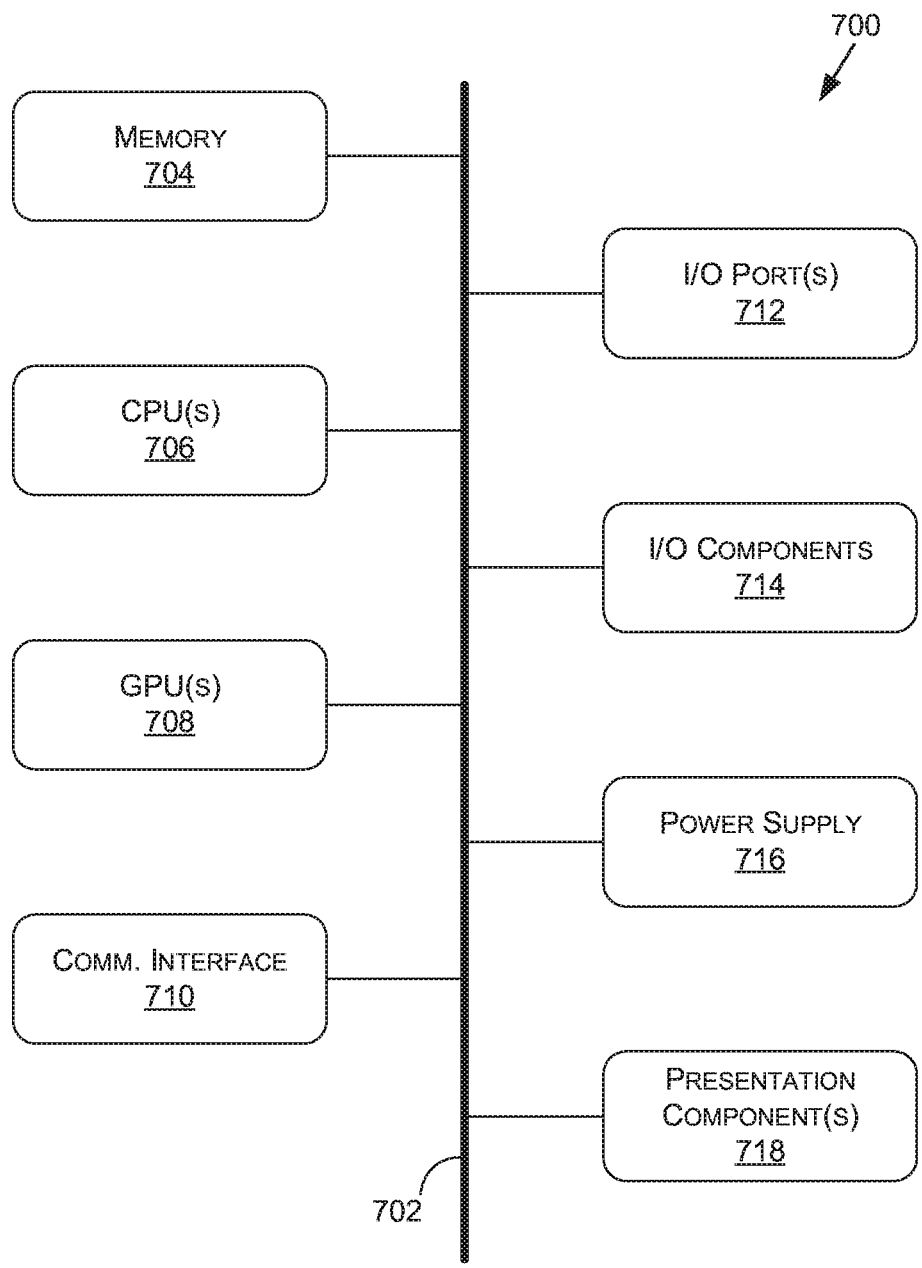
FIG. 7 is a block diagram of an example computing device suitable for use in implementing some embodiments of the present disclosure.

FIG. 7 is a block diagram of an example computing device 700 suitable for use in implementing some embodiments of the present disclosure. For example, some or all of the components of the computing device 700 may be included or used in the loupe system(s) 102, the local client device(s) 104, the server(s) 106, and/or the remote client device(s) 108, in addition to or alternatively from the other components or features described herein. The computing device 700 may include a bus 702 that directly or indirectly couples the following devices: memory 704, one or more central processing units (CPUs) 706, one or more graphics processing units (GPUs) 708, a communication interface 710, input/output (I/O) ports 712, input/output components 714, a power supply 716, and one or more presentation components 718 (e.g., display(s)).

Although the various blocks of FIG. 7 are shown as connected via the bus 702 with lines, this is not intended to be limiting and is for clarity only. For example, in some embodiments, a presentation component 718, such as a display device, may be considered an I/O component 714 (e.g., if the display is a touch screen). As another example, the CPUs 706 and/or GPUs 708 may include memory (e.g., the memory 704 may be representative of a storage device in addition to the memory of the GPUs 708, the CPUs 706, and/or other components). In other words, the computing device of FIG. 7 is merely illustrative. Distinction is not made between such categories as "workstation," "server," "laptop," "desktop," "tablet," "client device," "mobile device," "handheld device," "game console," "electronic control unit (ECU)," "virtual reality system," and/or other device or system types, as all are contemplated within the scope of the computing device of FIG. 7.

The bus 702 may represent one or more busses, such as an address bus, a data bus, a control bus, or a combination thereof. The bus 702 may include one or more bus types, such as an industry standard architecture (ISA) bus, an extended industry standard architecture (EISA) bus, a video electronics standards association (VESA) bus, a peripheral component interconnect (PCI) bus, a peripheral component interconnect express (PCIe) bus, and/or another type of bus.

The memory 704 may include any of a variety of computer-readable media. The computer-readable media may be any available media that may be accessed by the computing device 700. The computer-readable media may include both volatile and nonvolatile media, and removable and non-removable media. By way of example, and not limitation, the computer-readable media may comprise computer-storage media and communication media.

The computer-storage media may include both volatile and nonvolatile media and/or removable and non-removable media implemented in any method or technology for storage of information such as computer-readable instructions, data structures, program modules, and/or other data types. For example, the memory 704 may store computer-readable instructions (e.g., that represent a program(s) and/or a program element(s), such as an operating system. Computer-storage media may include, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which may be used to store the desired information and which may be accessed by computing device 700. As used herein, computer storage media does not comprise signals per se.

The communication media may embody computer-readable instructions, data structures, program modules, and/or other data types in a modulated data signal such as a carrier wave or other transport mechanism and includes any information delivery media. The term "modulated data signal" may refer to a signal that has one or more of its characteristics set or changed in such a manner as to encode information in the signal. By way of example, and not limitation, the communication media may include wired media such as a wired network or direct-wired connection, and wireless media such as acoustic, RF, infrared and other wireless media. Combinations of any of the above should also be included within the scope of computer-readable media.

The CPU(s) 706 may be configured to execute the computer-readable instructions to control one or more components of the computing device 700 to perform one or more of the methods and/or processes described herein. The CPU(s) 706 may each include one or more cores (e.g., one, two, four, eight, twenty-eight, seventy-two, etc.) that are capable of handling a multitude of software threads simultaneously. The CPU(s) 706 may include any type of processor, and may include different types of processors depending on the type of computing device 700 implemented (e.g., processors with fewer cores for mobile devices and processors with more cores for servers). For example, depending on the type of computing device 700, the processor may be an ARM processor implemented using Reduced Instruction Set Computing (RISC) or an x86 processor implemented using Complex Instruction Set Computing (CISC). The computing device 700 may include one or more CPUs 706 in addition to one or more microprocessors or supplementary co-processors, such as math co-processors.

The GPU(s) 708 may be used by the computing device 700 to render graphics (e.g., 3D graphics). The GPU(s) 708 may include hundreds or thousands of cores that are capable of handling hundreds or thousands of software threads simultaneously. The GPU(s) 708 may generate pixel data for output images in response to rendering commands (e.g., rendering commands from the CPU(s) 706 received via a host interface). The GPU(s) 708 may include graphics memory, such as display memory, for storing pixel data. The display memory may be included as part of the memory 704. The GPU(s) 708 may include two or more GPUs operating in parallel (e.g., via a link). When combined together, each GPU 708 may generate pixel data for different portions of an output image or for different output images (e.g., a first GPU for a first image and a second GPU for a second image). Each GPU may include its own memory, or may share memory with other GPUs. In some examples, the GPU(s) 708 may render graphics using various technologies, such as ray-tracing technologies, such as to generate the AR-content for display using the loupe system(s) 102.

In examples where the computing device 700 does not include the GPU(s) 708, the CPU(s) 706 may be used to render graphics.

The communication interface 710 may include one or more receivers, transmitters, and/or transceivers that enable the computing device 700 to communicate with other computing devices via an electronic communication network, included wired and/or wireless communications. The communication interface 710 may include components and functionality to enable communication over any of a number of different networks, such as wireless networks (e.g., Wi-Fi, Z-Wave, Bluetooth, Bluetooth LE, ZigBee, etc.), wired networks (e.g., communicating over Ethernet), low-power wide-area networks (e.g., LoRaWAN, SigFox, etc.), and/or the Internet.

The I/O ports 712 may enable the computing device 700 to be logically coupled to other devices including the I/O components 714, the presentation component(s) 718, and/or other components, some of which may be built in to (e.g., integrated in) the computing device 700. Illustrative I/O components 714 include a microphone, mouse, keyboard, joystick, game pad, game controller, satellite dish, scanner, printer, wireless device, etc. The I/O components 714 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing device 700. The computing device 700 may be include depth cameras, such as stereoscopic camera systems, infrared camera systems, RGB camera systems, touchscreen technology, and combinations of these, for gesture detection and recognition. Additionally, the computing device 700 may include accelerometers or gyroscopes (e.g., as part of an inertia measurement unit (IMU)) that enable detection of motion. In some examples, the output of the accelerometers or gyroscopes may be used by the computing device 700 to render immersive augmented reality or virtual reality.

The power supply 716 may include a hard-wired power supply, a battery power supply, or a combination thereof. The power supply 716 may provide power to the computing device 700 to enable the components of the computing device 700 to operate.

The presentation component(s) 718 may include a display (e.g., a monitor, a touch screen, a television screen, a heads-up-display (HUD), other display types, or a combination thereof), speakers, and/or other presentation components. The presentation component(s) 718 may receive data from other components (e.g., the GPU(s) 708, the CPU(s) 706, etc.), and output the data (e.g., as an image, video, sound, etc.).

The disclosure may be described in the general context of computer code or machine-useable instructions, including computer-executable instructions such as program modules, being executed by a computer or other machine, such as a personal data assistant or other handheld device. Generally, program modules including routines, programs, objects, components, data structures, etc., refer to code that perform particular tasks or implement particular abstract data types. The disclosure may be practiced in a variety of system configurations, including handheld devices, consumer electronics, general-purpose computers, more specialty computing devices, etc. The disclosure may also be practiced in distributed computing environments where tasks are performed by remote-processing devices that are linked through a communications network.

As used herein, a recitation of "and/or" with respect to two or more elements should be interpreted to mean only one element, or a combination of elements. For example, "element A, element B, and/or element C" may include only element A, only element B, only element C, element A and element B, element A and element C, element B and element C, or elements A, B, and C. In addition, "at least one of element A or element B" may include at least one of element A, at least one of element B, or at least one of element A and at least one of element B. Further, "at least one of element A and element B" may include at least one of element A, at least one of element B, or at least one of element A and at least one of element B.

The subject matter of the present disclosure is described with specificity herein to meet statutory requirements. However, the description itself is not intended to limit the scope of this disclosure. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

What is claimed is:

1. A method comprising:
   generating, using a camera disposed on a head-mounted device, image data representative of one or more images in a field of view of the camera;
   wirelessly transmitting the image data to a client device;
   wirelessly receiving, from the client device and based at least in part on a determination that a person is depicted in the image data, a signal;
   based at least in part on the signal:
   activating a light source disposed on the head-mounted device;

zeroing out one or more inertial measurement unit (IMU) sensors disposed on the head-mounted device;

estimating an amount of movement of the head-mounted device relative to a zeroed position based at least in part on sensor data generated using the one or more IMU sensors; and when the amount of movement is above a threshold, deactivating the light source.

2. The method of claim 1, wherein the head-mounted device includes eye-glasses coupled to a battery.

3. The method of claim 2, wherein the eye-glasses are coupled to the battery using ribbon wire.

4. The method of claim 1, wherein the determination that the person is depicted in the image data is by at least one of the client device or a server, and the determination is based on analyzing the image data using a facial recognition algorithm.

5. The method of claim 1, wherein the camera is electrically coupled to a housing discrete from the head-mounted device, the housing including a battery, a wireless communication interface, and at least one component associated with processing the image data.

6. The method of claim 1, wherein the one or more IMU sensors include at least one of a gyroscope or an accelerometer.

7. The method of claim 1, wherein, when a subsequent amount of movement indicates that the IMU sensors are within another threshold of the zeroed position, reactivating the light source.

8. The method of claim 7, wherein:
the image data is generated and transmitted continuously;
the generating and transmitting of the image data is suspended based at least in part on the one or more IMU sensors being zeroed; and
when the amount of movement is above the threshold, the generating and transmitting of the image data is resumed.

9. The method of claim 8, further comprising:
receiving a second signal from the client device and based at least in part on another determination that the person is depicted is subsequent image data generated after resuming the generating and the transmitting of the image data; and
reactivating the light source.

10. The method of claim 1, wherein the head-mounted device is part of a loupe system, and the head-mounted device further includes at least one loupe disposed thereon.

11. The method of claim 1, wherein the image data is stored on a server for retrieval by one or more remote client devices.

12. The method of claim 11, wherein the stored image data is retrieved via an application on the one or more remote client devices, the application being for educational purposes in viewing medical procedures from a perspective of a user of the head-mounted device.

13. A method comprising:
receiving, from a client device, image data generated by a camera disposed on eye-glasses of a loupe system communicatively coupled to the client device, the image data generated by the camera during at least a portion of a medical procedure;
determining one or more remote client devices authorized for viewing the medical procedure, the one or more client devices authorized based at least in part on an authentication procedure within respective instantiations of an application executing on the one more remote client devices;
encoding the image data to generate encoded image data; and
streaming the encoded image data to the one or more remote client devices to cause display of the encoded image data on respective displays of the one or more remote client devices.

14. The method of claim 13, wherein:
the eye-glasses include one or more loupes disposed thereon;
the one or more loupes having a magnification factor; and
a camera zoom is determined to correspond to the magnification factor.

15. The method of claim 13, wherein the client device is wirelessly communicatively coupled to the loupe system locally, and the server and the one or more remote client devices are remotely located with respect to both the client device the loupe system.

16. The method of claim 13, wherein the image data is further analyzed to determine whether a face of a person is present, and when the face of the person is detected, generating and transmitting a signal to the loupe system to cause a light disposed on the eye-glasses to activate a light source disposed thereon.

17. A loupe system comprising:
eye-glasses including:
one or more cameras disposed thereon to generate image data;
a light source disposed thereon; and
one or more inertial measurement unit (IMU) sensors;
a power device electrically coupled to the eye-glasses, the power device including:
a battery to power at least the one or more cameras and the light source; and
a wireless communication component to transmit the image data;
an application executing on a client device communicatively coupled to the power device, the application to:
determine, based at least in part on the image data, that a face of a person is represented by the image data; and
generate and transmit, via another wireless communication component of the client device, a signal to the power device, the signal causing the light source to be activated; and
wherein the one or more inertial measurement unit (IMU) sensors are zeroed to a zeroed position based at least in part on the signal being received by the power device.

18. The loupe system of claim 17, wherein the one or more IMU sensors include at least one of a gyroscope or an accelerometer.

19. The loupe system of claim 17, wherein:
sensor data generated by the one or more IMU sensors is tracked using one or more processors of the power device;
an amount of movement of the eye-glasses relative to the zeroed position is determined using the one or more processors and based at least in part on the sensor data; and
when the amount of movement is above a threshold, the light source is deactivated.

20. The loupe system of claim 17, wherein the eye-glasses further include at least one loupe disposed thereon.

* * * * *